United States Patent [19]

Silver et al.

[11] Patent Number: 4,970,298

[45] Date of Patent: * Nov. 13, 1990

[54] BIODEGRADABLE MATRIX AND METHODS FOR PRODUCING SAME

[75] Inventors: Frederick H. Silver, Long Valley; Richard A. Berg, Lambertville; Charles J. Doillon, Edison; Kevin Weadock, Piscataway, all of N.J.; Conrad Whyne, Edgewood, Md.

[73] Assignee: University of Medicine and Dentistry of New Jersey, Newark, N.J.

[ * ] Notice: The portion of the term of this patent subsequent to Oct. 27, 2004 has been disclaimed.

[21] Appl. No.: 875,827

[22] Filed: Jun. 18, 1986

Related U.S. Application Data

[63] Continuation-in-part of Ser. No. 843,828, Mar. 26, 1984, Pat. No. 4,703,108, which is a continuation-in-part of Ser. No. 593,733, Mar. 27, 1984, abandoned.

[51] Int. Cl.$^5$ ............................ A23J 1/10; C08H 1/06
[52] U.S. Cl. ..................................... 530/356; 523/105; 523/111; 424/485; 424/95.64; 128/DIG. 8

[58] Field of Search ................. 530/356; 128/DIG. 8; 524/17, 21; 523/105, 111; 527/201; 424/485, 94.64

[56] References Cited

U.S. PATENT DOCUMENTS

| | | | |
|---|---|---|---|
| 4,193,813 | 3/1980 | Chuapil | 530/356 |
| 4,440,680 | 4/1984 | Cioca | 530/356 |
| 4,522,753 | 6/1985 | Yannas et al. | 530/356 |

*Primary Examiner*—John Kight
*Assistant Examiner*—Nathan M. Nutter
*Attorney, Agent, or Firm*—Weiser & Stapler

[57] ABSTRACT

This invention relates to a biodegradable collagen matrix having a pore size and morphology which enhances the healing of a wound. It further relates to a process for preparing the matrix. One embodiment of the invention comprises a biodegradable matrix which comprises collagen, hyaluronic acid and fibronectin. Other embodiments include a process which comprises freeze drying a dispersion containing collagen, crosslinking the collagen via two crosslinking steps and freeze drying the crosslinked matrix.

31 Claims, 8 Drawing Sheets

BIODEGRADABLE MATRIX AND METHODS FOR PRODUCING SAME

This application is a Continuation-In-Part of pending U.S. Application Ser. No. 843,828, filed March 26, 1984 and now U.S. Pat. No. 4,703,108, which in turn is a Continuation of U.S. Pat. Application Ser. No. 593,733, filed March 27, 1984, now abandoned.

This invention relates to a biodegradable matrix, and more particularly to a multifunctional collagen-based matrix and/or carrier system thereof.

This invention further relates to a method for obtaining collagen matrices of the invention having a desirable pore size and morphology.

This invention further relates to a biodegradable matrix which, when placed on a wound, enhances the healing of the wound.

Delivery of drugs, growth factors, hormones, peptides and glycopeptides to external wounds has classically occurred by direct topical application and application to internal wounds by injection into the blood or by absorption into the blood through the digestive system. Controlled release of these agents has been achieved by encapsulation either in bulk or at a microscopic level using synthetic polymers, such as silicone, and natural polymers, such as gelatin and cellulose. The release rate can be controlled for periods of up to a year by proper choice of the polymeric system used to control the diffusion rate (Langer, R.S. and Peppas, N.A., Biomaterials 2,201,1981). Natural polymers, such as gelatin and cellulose slowly dissolve in a matter of minutes to hours while silicone remains intact for periods of months to years. Biodegradable polymers offer an advantage for controlled release to internal wounds since only a single surgical procedure is necessary.

Collagen is a biodegradable polymer found in animals and in man. It has been used as a plasma expander, vehicle for drug delivery, vitreous body replacement, hemostatic agent, suture material, corneal replacement, hemodialysis membrane, wound dressing and artificial skin, hernia patch, vessel prosthesis, vaginal contraceptive,, and injectable agent for tissue augmentation (Chvapil et al., Int. Review of Connective Tissue Research 6, 1, 1973; Chvapil, in Biology of Collagen edited by A. Viidik and J. Vuust, Academic Press, chapter 22, 1980). In most of these applications, the collagen is reconstituted and cross-linked into an insoluble form.

There is described in Yannas et al, (U.S. Pat. No. 4,060,081), the use of collagen and mucopolysaccharides as synthetic skin. Such material is cross-linked using glutaraldehyde, a bifunctional cross-linking agent, which reacts with free amines. One major drawback to using cross-linked collagen has been the adverse biological effects of free glutaraldehyde, a common agent used to cross-link and insolubilize collagen in many applications. Leaching of glutaraldehyde from cross-linked collagens has been shown to be cytotoxic to cells, specifically fibroblasts (Speer et al., J. Biomedical Materials Research 14,754,1980; Cooke et al., British J. Exp. Path. 64,172,1983). Recent evidence suggests that glutaraldehyde polymers and not monomeric glutaraldehyde form cross-links between collagen molecules; these cross-links can then rearrange to release free glutaraldehyde and glutaraldehyde polymers (Cheung, D.T. and Nimni, M.D., Connective Tissue Research 10,187–214,1982).

An object of the present invention is to provide a novel biodegradable matrix.

Another object of the present invention is to provide a novel collagen-based matrix.

Still another object of the present invention is to provide a novel collagen-based matrix in sponge or sheet form.

Yet another object of the present invention is to provide a novel biodegradable matrix impregnated with a carrier compound.

A further object of the present invention is to provide a novel biodegradable collagen-based matrix impregnated with a carrier compound.

Yet still another object of the present invention is to provide a novel biodegradable collagen-based matrix impregnated with a carrier compound in sponge or sheet form.

A still further object of the present invention is to provide a novel biodegradable collagen-based matrix impregnated with a carrier compound and is non-toxic and capable of promoting cell growth.

Yet another object of the present invention is to provide a novel biodegradable collagen-based matrix impregnated with a carrier compound for controlled release of drugs.

Yet still another object of the present invention is to provide a novel biodegradable collagen-based matrix impregnated with a carrier compound for topical application to external wounds.

Another object of the present invention is to provide a novel biodegradable collagen-based matrix impregnated with a carrier compound for application to internal wounds.

Another object of the present invention is to provide a method for producing a novel biodegradable collagen sponge or matrix having a desirable pore size and morphology.

Other worthwhile objects will become apparent from the disclosure herein. Other features and advantages of the invention will appear from the examples which follow and by referring to the appended Figures in which:

Figure 1:
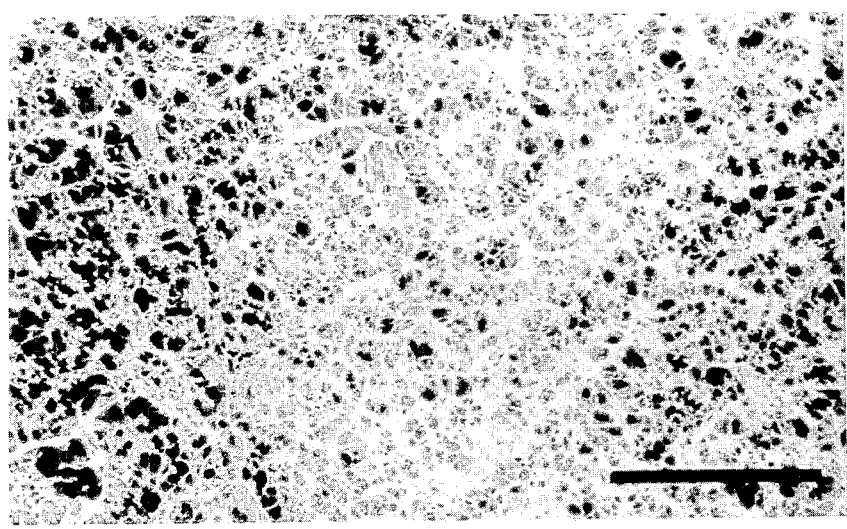
FIG. 1 is a scanning electron micrograph of an uncross-linked collagen sponge made from a 0.5% collagen (w/v) dispersion, at a pH of 2.5, and frozen at −90° C. Under these conditions collagen fibers with diameters of about 1 um are observed separated by pores of 15 um in diameter. (Bar=100 um).

These and other objects of the present invention are achieved in one embodiment by forming a sponge or sheet of a collagen-based material including a collagen selected from the group consisting of types I, II and III collagens which sponge or sheet is contacted with a cross-linking agent selected from the group consisting of a carbodiimide or a succinimidyl active ester to form an intermediate collagen-based matrix which is subsequently subjected to conditions of severe dehydration to form a collagen-based matrix in sponge or sheet form. In another embodiment, the sponge or sheet of the collagen-based material is first subjected to conditions of severe dehydration followed by contacting the thus formed intermediate collagen-based matrix with a carbodiimide cross-linking compound to form the collagen-based matrix in sponge or sheet form. In still another embodiment of the present invention the cross-linking agent is admixed with the collagen-based material prior to formation of the intermediate collagen-based sponge or sheet followed by processing steps of severe dehydration. In a particularly preferred form of the invention, a carrier compound is incorporated during processing to form a collagen-based matrix in sponge or sheet form impregnated with a carrier compound wherein the carrier compound is selected from the group consisting of types IV and V collagen, fibronectin, laminin, hyaluronic acid, proteoglycan, epidermal growth factor, platelet derived growth factor, angiogenesis factor, antibiotic, antifungal agent, spermacidal agent, enzyme and enzyme inhibitor.

The collagen-based carrier systems of the present invention are based on the use as a starting material of a soluble or insoluble collagen selected from the group consisting of types I, II and III collagens and mixtures thereof.

Soluble collagens of the types I, II and III collagen are prepared by limited enzymatic digestion of tissue enriched in such collagen types and are formed into collagen-based solution (i.e. a soluble collagen dissolved in a suitable solvent, such as dilute hydrochloric acid, dilute acetic acid or the like).

Insoluble collagens are derived from the following typical sources: type I collagen; bovine, chicken and fish skin, bovine and chicken tendons and bovine and chicken bones including fetal tissues; type II collagens; bovine articular cartilage, nasal septum, sternal cartilage; and type III collagen; bovine and human aorta and skin.

In one embodiment of the present invention, a collagen-based solution or an insoluble collagen dispersed and swollen in a suitable liquid media (e.g. dilute hydrochloric acid, dilute acetic acid or the like) is subjected to a temperature of between about 0° C. to −100° C. to thereby solidify the collagen-based material. Thereafter, the solidified collagen-based material is subjected to a vacuum of less than about 50 millitorr at a temperature of from about 22° C. to −100° C. to form a collagen-based sponge to be further processed, as hereinafter more clearly described. Generally, a weight ratio of soluble or insoluble collagen to solvent or dispersion agent, respectively, of from 1 to 10,000 or from 1 to 15 is used to form the collagen-based solution or dispersion.

In another embodiment of the present invention such a collagen-based solution on a collagen-based dispersion is dried into sheet form prior to further processing as more fully hereinafter described. Drying is effected at temperatures of from 4° C. to 40° C. for a period of time of from 2 to 48 hours.

In one embodiment of the present invention to form a collagen-based matrix, a collagen-based sponge or sheet is first contacted with a cross-linking agent selected from the group consisting of a carbodiimide or N-hydroxysuccinimide derived active esters (succinimidyl active ester) followed by severe dehydration to form the collagen-based matrix.

In another embodiment of the invention, a collagen solution or an insoluble collagen is dispersed in an acid medium at a pH between about 3.0 and 5.0 and frozen at a temperature between about −30° C. and −50° C. The dispersion is then freeze-dried to obtain a collagen sponge.

In a further embodiment of the invention, a collagen solution or collagen dispersion is an acid medium at a pH between 3.0 and 5.0 is frozen at a temperature between about −30° C. and −50° C., freeze-dried then subjected to two crosslinking steps selected from the group of dehydrothermal crosslinking and cross-linking with carbodiimide or succinimydyl ester/carbodiimide. The cross-linked sponge is then placed again in acid medium at pH from about 3.0 to about 5.0, frozen at about −30° C. to −50° C. and freeze-dried. In this manner, a collagen sponge having a desired pore and channel structure is formed by freeze-drying, the pores and channels are permanently formed within the matrix by cross-linking and the sponge in its final form is obtained by the additional freeze-drying step to reform collapsed pores and channels.

Examples of the carbodiimides include cyanamide and 1-ethyl-3-(3-dimethylaminopropyl)-carbodiimide hydrochloride. Examples of bifunctional succinimidyl active esters including bifunctional N-hydroxysuccinimide, 3,3$^1$-dithio(sulfosuccinimidyl) proprionate and bis (sulfosuccinimidyl) suberate. When using a carbodiimide cross-linking agent, the collagen-based sponge or sheet is immersed in a carbodiimide solution at a concentration of from about 0.1 to 10% (W/V) maintained at a temperature of from about 2° C. to 40° C. and at a pH of between 2 to 11 for a period of time of from about 2 to 96 hours. When using a succinimidyl active ester cross-linking agent, the collagen-based sponge or sheet is immersed in a solution thereof at a concentration of from about 0.1 to about 15.0% (W/V) maintained at a temperature of from about 2° C. to 40° C. for a period of time of from about 2 to 96 hours. The collagen-based sponge or sheet is placed in a solution containing 0.1 to about 15% (W/V) of N-hydroxysuccinimide and carbodiimide at a pH between 2 to 11 for a period of time between 2 to 96 hours at a temperature of from about 2° C. to 40° C. The thus treated intermediate collagen-based matrix is exhaustively washed to remove excess cross-linking agent.

Severe dehydration of the intermediate collagen-base involves conditions of temperatures of from 50° C. to 200° C. at a vacuum of 50 millitorr or less for a period of time of from 2 to 96 hours to thereby form the collagen-based matrix. Prior to severe dehydration, the intermediate collagen-based matrix in sponge form is preferably solidified at a temperature of between about 0° C. to −100° C. and thereafter subjected to a vacuum of at least 50 millitorr at a temperature of between about 22° C. and −100° C.

In another embodiment of the present invention to form the collagen-based matrix when using a carbodiimide cross-linking agent, severe dehydration may be effected to form an intermediate collagen-based matrix prior to contracting such an intermediate collagen-based matrix with such a cross-linking agent.

In another embodiment of the present invention to form the collagen-based matrix, the cross-linking agent is premixed with the collagen-based material prior to drying or initiating of freeze drying processing steps.

The collagen-based matrix prepared in accordance with the present invention may be described as a "coral-like" or "scaffold" structure having interstices of a pore size of from 3 to 100 um, and of a molecular weight of from $10 \times 10^6$ to in excess of $50 \times 10^6$ with a molecular weight between cross-links from 1,000 to 100,000 via the formation of covalent bonds.

Another embodiment of the present invention is the incorporation of a carrier compound into the collagen-based matrix. Such a carrier compound is selected from the group consisting of collagen types IV and V, fibronectin, laminin, hyaluronic acid, proteoglycans, epidermal growth factor, platelet derived growth factor, angiogenesis factor, antibiotic, antifungal agent, spermicidal agent, hormone, enzyme and enzyme inhibitor.

Generally, the carrier compound may be introduced at any time during processing of the collagen-based material to the collagen-based matrix in sponge or sheet form. Preferably, a carrier compound is incorporated prior to solidifying of the soluble or insoluble collagen in forming the intermediate collagen-based matrix, or prior to solidifying of the intermediate collagen-based matrix prior to severe dehydration. The carrier materials are added in an amount of from 1 to 30% (w/w) based on the weight of soluble or insoluble collagen. Generally, connective tissue factors, such as fibronectin, types IV and V collagens, laminin, glycosaminoglycans and hyaluronic acid are incorporated during initial processing steps in forming the collagen-based sponge, or after cross-linking of the intermediate collagen-based matrix. It is preferable to incorporate fibronectin and hyaluronic acid during forming of the intermediate collagen-based matrix.

In another embodiment of the present invention to form the collagen-based matrix of the invention, hyaluronic acid and fibronectin are progressively mixed with collagen during dispersion, prior to the two cross-linking steps.

There are many sources for the diverse carrier compounds for incorporation into the collagen-based matrix constituting one embodiment of the present invention. Type IV and V collagens are found associated with basement membranes and smooth muscle cells in tissues, respectively. Typical sources of Type IV include the EHS mouse sarcoma tumor, bovine and human placenta, lens capsule and kidney; sources of Type V collagen include placental membranes, ocular tissues and fetal skin (see for example, Trelstad, In Immunochemistry of the Extracellular Matrix, Vol. 1 edited by H. Furthmayr, CRC Press, chapter 2, 1982).

Typical sources of proteoglycans include bovine and human cartilage and synovial fluid, nasal septum and sternal cartilage, and skin. Typical sources for glycoproteins include EHS tumor, bovine and human kidneys, cartilage, bone and placenta as well as bovine and human blood. Typical sources of hyaluronic acid include rooster comb and bovine vitreous.

Preferred carrier compounds for the collagen-based matrix include fibronectin, laminin, type IV collagen and complexes of hyaluronic acid and proteoglycans. A value of the swelling ratio of between 2.5 to 5 is required for a collagen-based matrix which comes into contact with open wounds, while a swelling ratio of between 2.5 to 10 are useful for a collagen-based matrix including carrier compounds for subcutaneous implantation. The swelling ratio is defined as the volume of water absorbed per unit volume of collagen-based matrix.

In the case of internal wounds and short-term drug release, collagen-based matrix including a carrier compound in the form of a sheet or a tube is placed in direct contact with tissue.

The biodegradation rate and the release rate can be controlled by variation of the cross-link density. For applications where long-term release is desired, a nonporous diffusion layer of a biodegradable polymer, such as poly-3(hydroxybutyrate) is applied to each side of the collagen-based matrix. For materials to be used on full thickness wounds, a diffusion control layer, such as described in the aforementioned U.S. Letters Patent to Yannas, is applied to prevent diffusion of water or other small volatile molecules from the collagen-based matrix; the diffusion control layer must adhere tightly to the collagen-based matrix layer. The combination of collagen-based matrix layer and diffusion control layer must be strong enough to be sutured and have a tensile strength of at least 100 psi and be able to deform at least 10% before failing. Synthetic non-biodegradable polymers, such as silicone polymers (Silastic Medical Grade Adhesive) or biodegradable polymers, such as polylactic acid, polyglycolic acid, poly-3(hydroxybutyrate) and copolymers of these materials can be used as the diffusion control layer.

Silicone polymers are preferred materials to control the rate of diffusion of small molecules. Curing of the adhesive in the diffusion control layer can occur without wetting the carrier compound in the collagen-based matrix by dessication at room temperature. A film 0.5 to 1.5 mm in thickness is applied to the matrix layer and is allowed to cure at room temperature for at least 2 hours using a vacuum of 14 in. of Hg.

The thickness of the collagen-based matrix can be varied from 0.5 to several hundred mm. A preferred range is from about 0.5 to 5 mm. For full thickness wounds, a thickness of 2 to 3 mm is desired and enables close contact between the carrier compound in the collagen-based matrix and the wound bed.

When implanted subcutaneously or directly on full thickness dermal wounds, any collagen-based matrix of the present invention does not stimulate the inflammatory process. In addition, chronic implantation results in fibroblast and endothelial cell migration into the collagen-based matrix. The degradation and resorption rate of collagen-based matrices are as assayed in vitro by determination of the time that 1 mg of the material resists solubilization by 100 units of bacterial collagenase. One unit of collagenase liberates amino acids in collagen equivalent to 1.0 micro mole of L-leucine in 5 hours at 37° C. A combination of succinimidyl active ester formation and severe dehydration or carbodiimide treatment and severe dehydration increases the collagenase resistance time significantly over that observed by any of the procedures heretofore used. These studies indicate that the cross-linking methods of the present invention result in resistance to collagenase degradation and show no stimulation of inflammation.

Temporary or permanent wound dressings that are designed to enhance wound healing are needed to cover large open wounds on patients with extensive burns or pressure ulcers. The utility of collagen-based materials in wound repair has been summarized by Chvapil (supra. J. Biomed. Mat. Res., 11, 721-741 (1977); J. Biomed. Mat. Res., 16, 245-263 (1982)). Collagen's high tensile strength, low extensibility, fiber orientation, controllable crosslinking, low antigenicity, effects on wound healing and blood coagulation are of principal importance. Furthermore, its ability to be produced in a variety of forms such as sheets, tubes, sponges and powder is important in the production of useful medical products. In vivo studies show that the use of a collagen-based sponge allows cell migration, (Chvapil supra (1977)), inhibits wound contraction, (Yannas et al J. Biomed. Mat. Res., 14, 65-81 (1980), and accelerates wound repair (Doillon et al, Scanning Electron Microscopy 1984, III, 1313-1320). An additional advantage of using a collagen sponge is that wound fluids can be better controlled (Chavpil supra, 1982).

Cellular response to collagen-based materials is a consequence of the purity, type of chemical modification required for crosslinking or attachment of other molecules and the surface morphology. Cell growth on collagen in cell culture is dependent on the three dimensional structure, (Fisher and Solursh, Exp. Cell. Res., 123, 1-14 (1979)). Cells, particularly fibroblasts, grown on collagen sheets do not retain their morphology seen in vivo and appear to require a three dimensional substrate for growth (Dunn and Ebsendal, Exp. Cell Res., 111, 475-479 (1978); Schor and Court, J. Cell Sci., 38, 267-281 (1979); Grinnell and Bennett, Methods in Enzymology Academic Press, N.Y., 1982, Vol. 82, pp. 535-544). Esdale and Bard (J. Cell Biol., 54, 626-637 (1972) have shown that collagen substrates in the form of hydrated collagen gels are the best material for maintaining cells in culture. This material has a fibrillar structure and cells retain their natural in vivo shape and mobility and continue to spread in this environment (Grinnell and Bennett; Esdale and Bard, supra). Fibrillar structure appears to be an important parameter in the design of a biomaterial as well as porous structure allowing tissue ingrowth into the material. Such a collagen matrix is obtained by dispersing collagen in an acid solution, freezing the dispersion and then freeze-drying the dispersion to form a sponge.

Scanning electron microscope (SEM) studies have been conducted on collagen sponges to determine the factors that influence pore size and matrix configuration. Pore size has been controlled by varying the concentration of the collagen dispersion, and varying the conditions of freeze drying.

Unexpectedly another approach to control pore size, fibrillar structure and uniformity of collagen sponges has been discovered. These factors of fibrillar structural and uniformity of the sponge have been varied by changing the extent of fiber dispersion, the pH of the collagen dispersion, and the freezing temperature.

Cellular ingrowth within a collagen sponge or matrix depends on the porosity and the presence of fibrous structure. Collagen sponges are made by freezing and then freeze-drying collagen dispersions under acidic conditions. The dispersion pH, viscosity and freezing temperature affect the surface and bulk morphology of collagen-based sponges.

Using scanning electron (SEM) and light microscopy to study the effects of these factors, it has been discovered that large surface pores which form connections (channels) with the interior of the sponge are formed using low viscosity collagen dispersions. At high dispersion pH (3.2) and at moderate freezing temperature ($-30°$ C.) fibrous structure and a large number of channels are present. Using a lower dispersion pH (2.0) and freezing temperature ($-80°$ C.) pore sizes are smaller with channels and fibrous structure while higher freezing temperature ($-20°$ C.) results in sheet-like structure and increased pore size.

Differences in pore size and surface morphology are explained on the basis of ice crystal growth. In the case of abundant free water (high pH) and high freezing temperature, the pore size is greatest due to enhanced ice crystal growth.

SEM observations of the air side of collagen-based sponges produced by freeze-drying unexpectedly show a non-porous surface which does not support ingrowth of wound tissue. Previous studies have not described this phenomen (Dagalokis et al, J. Biomed. Mat. Res., 14, 511-528 (1980)). During freezing and freeze-drying procedures, temperature differences between air and pan sides can explain differences in surface morphology. Temperature variations are more important on the air side since it is the last part of the sponge to freeze and therefore can undergo the greatest degree of collapse.

During freezing, separation of collagen fibers by ice crystal growth can explain the preservation of network of collagen fibers. Fast freezing and separation of collagen fibers can be facilitated by rapid cooling induced by the rod-like form of collagen. This leads to the formation of channels which connect surface pores and the interior of the sponge. It has been demonstrated using elongated and polymerized molecules such as dextran and gelatin that the rate of cooling is faster than with other molecular forms (MacKenzie, Ann, N.Y. Acad. Sci., 125, 522-547 (1965)). In contrast, large ice crystal growth during slow freezing at high temperature ($-30°$ C.; −20° C.) results in the formation of a sheet-like structure of aggregated collagen fibers with pores that do not connect to form channels. Freezing experiments show that a critical bath temperature and freezing rate is required for optimized ice crystal growth. Fast freezing at low temperature induces cracking, uniform small channels, and the production of a fibrous structure. Slow freezing at higher temperatures results in nonuniformity, large pores with more collapsed pores than continuous channels.

Unorganized ice crystal growth can induce irregular sublimation with recrystallization of water vapor and secondary sublimation in the same areas during the freeze-drying procedure. This phenomen can explain in part the partial collapse of pores during freeze-drying and formation of sheet-like structures. On the other hand, channel structure can be due to a more regular linear ice crystal growth and consequently to a regular sublimation between the surface and the interior of the sponge without recrystallization of the water vapor, leaving a continuous open structure.

The results also show that other variations can modify the surface morphology. During dispersion of collagen, water in the collagen solution is composed of water bound to the molecule and free water. Free water is submitted to the ice crystallization while bound water is normally more mobile (MacKenzie, supra.). This suggests that during dispersion of collagen, a dispersion with thick collagen fibers has more free water as opposed to a dispersion with fine fibers that is obtained after extensive dispersion. This leads to the prediction that the porous structure which arises from ice crystals would be larger in the presence of large fibers as opposed to small fibers. In addition, large channel and pore sizes, and fibrous structures are observed when the pH of the dispersion was increased. These variations can be due to the difference in ratio between free and bound water. Indeed, as the pH decreases, the collagen swells more and binds more water, consequently, free water forms small ice crystals during freezing and induces small pores during the freeze-drying procedure.

No significant difference is observed between freeze-dried specimens observed directly by SEM and wet collagen sponges observed after fixation and critical point drying procedures. Thus, the cross-linking procedure used in the present invention is stable and does not result in the shrinkage of pores and channels. In additon, plastic embedding techniques do not significantly result in shrinkage of the pores in the collagen sponges.

All these variations must be considered in the manufacture of a collagen-based sponge. In the collagen-based model of the invention, the optimum conditions for sponge formation are: (1) to avoid excessive blending and obtain a well dispersed mixture of large collagen fibers, (2) to use a pH of about 3.0 to about 4.0, (3) to freeze the collagen dispersion to from about −30° C. to about −50° C. in an ethanol bath, and (4) the ethanol bath must be in direct contact with the plastic or metal tray to avoid any air gap. Following these steps, collagen sponges are obtained in a uniform state with average pore sizes which allow tissue ingrowth. A fibrous structure associated with an average pore size of 50 to 250 um and, preferably 100 um ± 50, containing channels is an ideal structure for a collagen-based material for tissue ingrowth. A pore size of about 100 um corresponds to the geometry which can modify fibroblast behaviour as already described (Chvapil, J. Biomed Mat. Res., 11, 721–741 (1977), Ramachandran and Reddi, *Biochemistry of Collagen*, Plenum Press, N.Y., 1976, 449–478 and Dagalakis, supra.). Studies on animals show that tissue ingrowth into the sponge occurs when pore sizes are between 50 to 300 um (Doillon et al, Biomaterials, Vol. 7, January 1986, pp. 4–7).

The upper surface of the sponge in direct contact with the atmosphere during the freeze-drying process, called the "air side", is found to have a collapsed form or a sheet-like structure in almost all cases. For this reason the other side, in direct contact with either plastic or metal tray, called the "pan side", was studied. It is observed to exhibit a variation of structure defined above. At high magnification (×24,000), SEM observations show collagen fibrils with diameters between 100 and 300 nm, and fibers with diameters between 700 nm and 1200 nm.

The morphology of the pan side of collagen sponges is studied by varying the freezing temperature and pH. It has been determined that the rate of freezing and surface morphology also depended on the nature of the support used to freeze the collagen dispersion. It has been determined that when the thin plastic boats were placed in contact with a metal plate at the desired temperature the rate of freezing is greater than that observed when the dispersion is frozen in a plastic coated metal try. When metal trays are used the freezing temperature is diminished 10° C. to obtain similar surface morphology.

Using thin plastic boats and an 0.5% (w/v) collagen dispersion the effects of freezing and pH on surface morphology were investigated. Freezing at temperatures of −80° C. and below occured so rapidly that the sponge invariably cracked. Intact sponges could not be made at temperatures of −80° C. and below, and data obtained on the surface morphology was obtained on intact pieces of sponge. Sponges made at these temperatures are uniform and are fibrous in nature (FIG. 1). The average pore size is between 3 and 15 um and is listed in Table I.

Freezing at temperatures between −60° C. and −80° C. results in a uniform sponge morphology composed of both collagen fibers and pores. However, if the sponge is kept in the freezing bath for a prolonged time after it was frozen, cracking occurs in about 25% of the samples.

When sponges are frozen at a temperature between −40° C. and −60° C. no cracking is observed. Sponges frozen in this temperature range are uniform and retain a fibrous structure. Pore and channel sizes increase to 27 um at a freezing temperature of −55° C.

Figure 2:
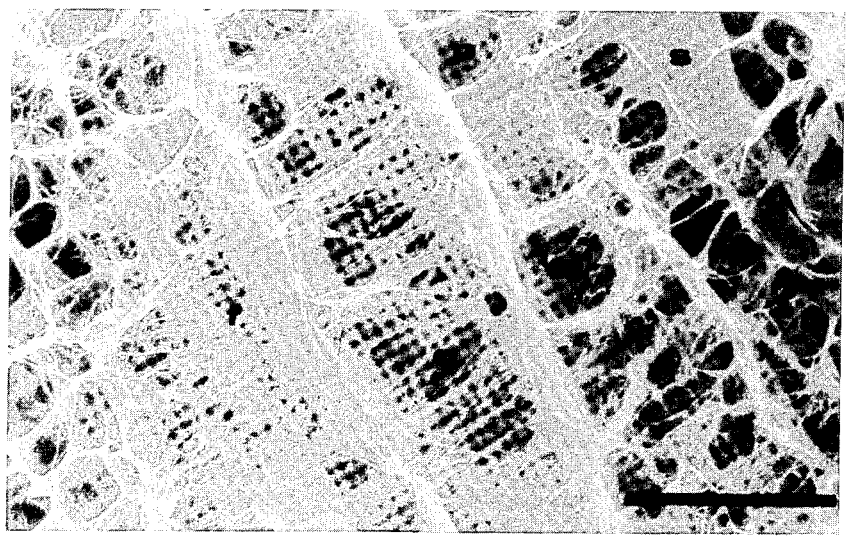
FIG. 2 is a scanning electron micrograph of an uncross-linked collagen sponge made from a 0.5% collagen (w/v) dispersion, at a pH of 3.25, and frozen at −30° C. in an ethanol bath. This structure contains a small number of pores (p), and sheet-like structure (s), and a large number of collagen fibers (f) and channels (c). (Bar=100 um).

Slow freezing of collagen dispersions is accomplished at temperatures between −20° C. and −40° C. At this temperature the gross surface morphology is sensitive to the smoothness of the freezing surface. At this temperature small temperature gradients across the freezing surface cause nonuniformity of surface morphology; the best results are obtained when the dispersion is frozen in an ethanol bath (FIG. 2). At −30° C. the range of pore sizes varies from 36 to 125 um with an average of about 64 um.

Figure 3:
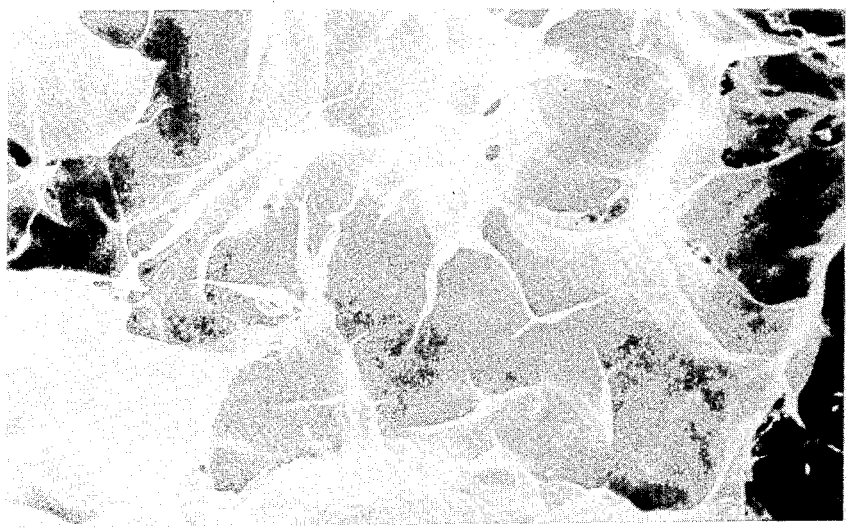
FIG. 3 is a scanning electron micrograph of an uncross-linked collagen sponge made from a 0.5% collagen (w/v) dispersion at pH 2.0, and frozen at −30° C. Under these conditions a porous sheet-like structure is formed. (Bar=100 um).

The effect of the dispersion pH on sponge morphology is not significant at temperatures below −350° C. However, the effect of pH is significant between −35° C. and −20° C. At these temperatures and using a dispersion pH of 2.0, a small amount of fibrous material is present but the bulk of the collagen exists in a sheet-like structure with surface pores. In comparison, at pH 3.5 sponges are more fibrous and have less collagen in sheet-like structures with more channels present. Varying the pH from 2.0 to 3.75 changes the surface morphology from a porous sheet-like structure (FIG. 3) to a predominantly fibrous structure. Associated with increased pH from pH 2.0 to 3.75 at −30° C. is increased pore and channel average sizes of about 150%.

A collagen sponge of the optimum structure, to aid in the healing of a wound, has pores throughout the sponge which are of relatively uniform size. The pores are interconnected by channels. These channels connect the surface pores with the pores which are located within the interior of the sponge. The pores have a size of from about 50 to about 250 um, more preferably about 100 ± 50 um. To obtain a sponge of the optimum structure, the pH of the dispersion is between about 3.0 and about 5.0 and more preferably between about 3.0 and about 3.5 and the freezing temperature is between about −30° C. and about −50° C. and more preferably between about −30° C. and −40° C.

When the collagen concentration of the dispersion is increased from 0.5% (w/v) to 1.0% (w/v) the morphology exhibits similar freezing temperature and dispersion pH characteristics described above with no statistical differences observed. However, increased concentration (1.0% w/v) results in smaller average sizes of pores.

The variation of the speed and time of blending of the collagen dispersion affects the surface morphology of collagen sponges. After a slow blending for 1 minute a low viscosity dispersion is obtained and results in fibrous structure and channels with an average size of 300 um. After long blending times (3 to 5 minutes) at high speeds a viscous dispersion is obtained and results in small pore sizes (30 um) with more surface pores present. Few channels and sheet-like structures are present under these conditions.

Figure 4:
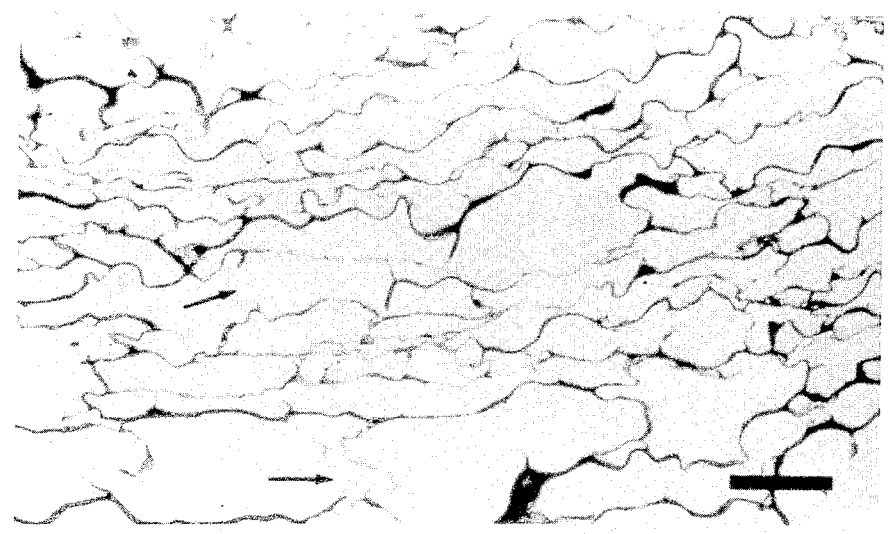
FIG. 4 is a micrograph of a section of a collagen sponge observed by light microscopy showing the connection between pores and channels which are marked by arrows. (Bar=100 um).

The morphology of the sponge interior was studied at the light microscopic level on sections of plastic-embedded collagen sponges (FIG. 4). Channels essentially are closed by bundles of collagen fibers. Channel sizes measured based on light microscopy are about 83% of those observed by SEM.

Repair of large open wounds involves the formation of granulation tissue which is initially characterized by the presence of thin unorganized collagen fibers (Williams, 1970, J. Pathol. 102, 61-68; Ross and Benditt, 1961, J. Biophys. Biochem. Cytol. 11, 677-700) associated with non-collagenuous interfibrillar material (Kischer, 1974, Amat. Rec. 179, 137-146; Kischer and Shetlar, 1974, Connective Tissue Res. 2, 205-213). Later, during the remodeling phase large collagen fibers composed of thicker fibrils are observed. During the remodeling phase of wound closure, the thickness of the collagen fibers is observed to increase but never reaches that observed in normal dermis (Levenson et al., 1965, Amn. Surg. 161, 293-308; Gillman, 1968; Knapp et al., 1977, Am. J. Pathol. 86, 47-63; Williams, supra.). The tensile strength of the repair of dermal wounds is related to the amount of collagen (Levenson et al., supra.) and never reaches that of normal skin. It has now been found that increased organization of collagen in fibers is related to increased wound tensile strength.

In the case of immature healing, excessive remodeling results in hypertrophic scar tissue which is characterized by whorls containing randomly deposited collagen that is eventually aligned parallel to flexion lines of the scar (Linares et al., 1972, J. Invest. Dermatol., 59, 1323-331). Transmission electron microscopy shows slightly irregular to ovoid fibrils with diameters less than normal (Kischer, supra.) and an excess of glycosaminoglycans associated with collagen fibrils (Linares et al, supra., and 1973, J. Trauma, 13, 70-75). By scanning electron microscopy (SEM), collagen fibers are rarely found and appear as a homogeneous mass of material in hypertrophic scar tissue (Kischer, supra.); however, when tension is applied, collagen fibrils can be identified by SEM (Kischer and Shetlar, supra.). The apparently reduced extensibility of hypertrophic scar tissue (Dunn et al., 1985, J. Invest. Dermatol, 84, 9-13) is a result of partial pre-alignment of the collagen fibers (Kischer and Shetlar, supra.).

Collagen-based materials have been used as a scaffold for tissue ingrowth to improve wound healing. Type I collagen supports fibroblast attachment and growth in vitro (Kleinman et al., 1981, J. Cell Biol., 88, 473-485) and in vivo (Yannas et al., 1982, Science, 215, 174-176) and is associated with the spatial deposition of newly formed collagen fibers (Doillon et al., 1984, Scanning Election Microsc., III, 1313-1320). Collagen fibers formed in wounds in the presence of collagen-based materials are oriented, uncrimped and have larger diameters than tissue formed in the absence of the sponge, as observed by SEM.

Other components of the extracellular matrix induce cell mobility and attachment in vitro. Fibronectin (FN) is known to increase chemoattraction and spreading of fibroblasts in vitro (Gauss-Muller et al., 1980, J. Lab. Clin. Med., 96, 1071-1080; Kleinman et al., supra.), and is found in large amounts during embryonic skin development (Gibson et al., 1983, J. Invest. Dermatol, 81, 480-485) and in healing wounds (Grinnell et al., 1981, J. Invest. Dermatol., 76, 181-189). Hyaluronic acid (HA) is found in high concentrations during embryonic skin development, and is associated with cell movement and differentiation (Fisher and Solursh, 1977, J. Embyro. Exp. Morphol., 42, 195-207; Toole, 1982; Kujawa and Tepperman, 1983, Dev. Biol., 99. 277-286). It appears as one of the first extracellular matrix macromolecules synthesized during wound healing (Alexander and Donoff, 1980, J. Surg. Res., 29, 422-429).

Using SEM and specific staining techniques, the analysis of collagen deposition and remodeling that occurs in a collagen-based sponge in the presence of fibronectin and hyaluronic acid was undertaken. The goal was to determine if these factors enhance wound healing.

Unexpectedly, in the presence of HA and FN, the morphology of a collagen-based sponge is modified such that interchannel connections are more numerous and is associated with increased tissue ingrowth. Additionally, HA and FN can enhance wound healing by increasing collagen fiber diameters through their known physiological actions. The fibroblast numbers and collagen deposition during tissue ingrowth can be increased in the presence of HA and FN and is associated with the organization of collagen fibrils into fibers.

The preferred concentration of both HA and FN in a sponge which is a matrix of collagen fibers is from about 0.1% by weight to about 4% by weight for each component. More preferably, the range is from about 1% to about 2% for each component. Most preferably the matrix contains about 1% of each of HA and FN.

In the presence of a collagen-based material, deposition and orientation of collagen is similar to that observed in sutured wounds, except that collagen fiber diameters are thicker in the presence of the collagen-based material at earlier times than in sutured wounds.

SEM observations of sutured wounds on rats (Levenson et al., supra.) and guinea pigs showed average collagen fiber diameters of 3 um ±1 at day 14 post wounding. Wound healing within a collagen-based sponge is similar to that within wounds that are sutured closed except the time lag for collagen fiber deposition observed in the absence of a collagen-based sponge is greater.

In the presence of HA and FN the time lag for deposition of newly assembled collagen fibers within the collagen sponge is decreased. Increased birefringence in the presence of HA and FN reflects increased collagen deposition. HA and FN enhance collagen deposition during the early phase of wound repair by attraction of increased numbers of fibroblasts.

Figure 5A:
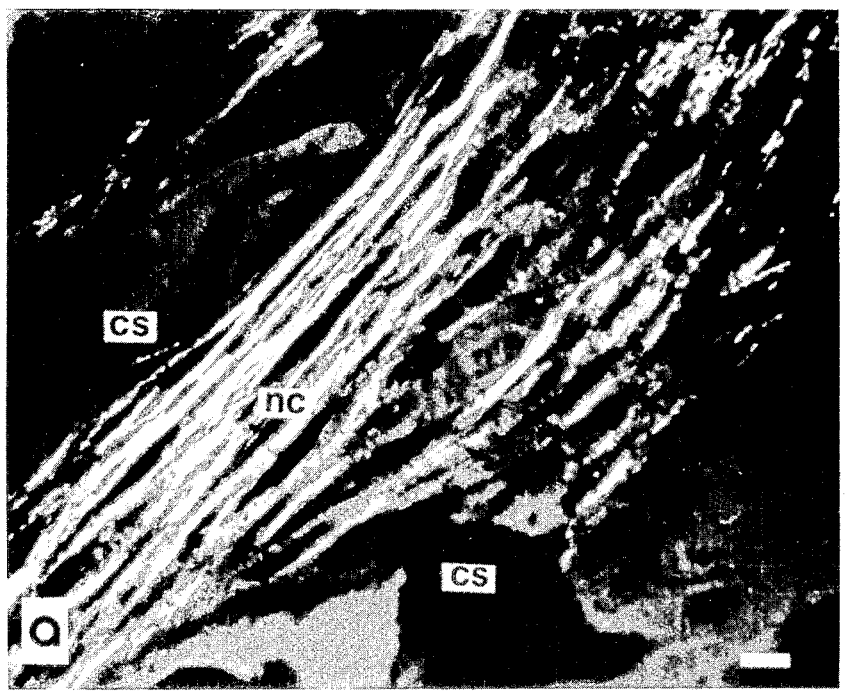
FIG. 5 shows micrographs of picro-sirius red stained tissue sections observed under polarized light. The birefringence of the newly formed collagen (NC) is oriented following the bundles of the collagen sponge (CS). At day 9 post-implantation, the birefringence is less in the control collagen sponge (a) than in the collagen sponge associated with hyaluronic acid and fibronectin (b). (Bar = 10 um).
Figure 5B:
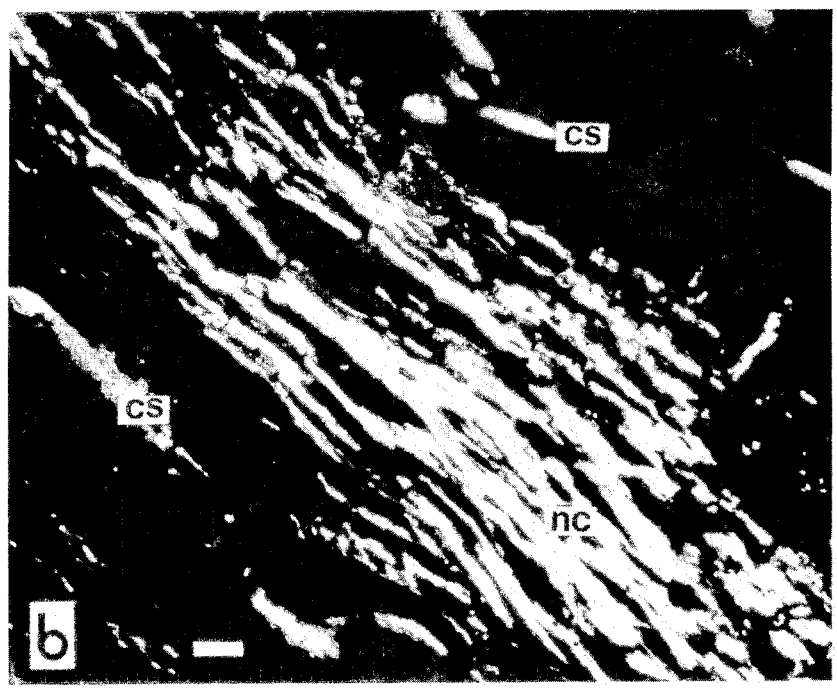

Histological sections showed new tissue ingrowth into the collagen-based sponges, but uniform ingrowth into the sponge was not found in all the samples. Good tissue ingrowth was defined as a tissue rich in fibroblasts (Table II) and dense in newly synthesized collagen determined by Masson's trichrome. Good ingrowth was found when the collagen sponge was associated with 1% FN and 1% HA (HAFN collagen sponge) and with a collagen sponge in the presence of 5% HA at days 6, 9, and 12 and with a collagen sponge in the presence of 1% FN at days 9 and 12. Large amounts of FN alone (5%), small and large amounts of HA (1% and 10%), and increased amounts of both HA and FN resulted in less than optimal tissue ingrowth within the collagen sponge (Table II) and that picro-sirius red staining showed orientation of the newly formed uncrimped collagen fibers parallel to the collagen bundles of the sponge as previously described (Doillon et al., supra.). This orientation of densely stained fibers was more frequently observed within the collagen sponge containing HA and FN and the brightness was greater than in the control group (see FIG. 5), and more particularly within the sponge containing 1% HA and 1% FN.

Below the sponge granulation tissue was progressively organized into crimped fibers. However, unexpectedly this was rarely observed below the sponges with 1% HA and 1% FN (HAFN collagen sponge) where a thin granulation tissue was seen.

The number of fibroblasts inside the sponge (Table IIIA) was similar for all sponges. However, in the presence of 1% HA+1% FN, the ingrowth of fibroblasts was found to be significantly higher ($p < 0.0001$) than in the other sponges tested. The number of fibroblasts was unchanged with increased time post-wounding; but for each time period there was a significant different ($p < 0.024$) between the different treatments of the sponge.

The brightness inside the sponge (Table IIIB) was significantly increased in the presence of both 1% HA +1% FN ($p < 0.0001$). In the other sponges tested with good ingrowth, the brightness increased significantly between days 8 and 12 ($p < 0.0001$).

In the granulation tissue formed between the wound bed and the sponge, the number of fibroblasts was independent of treatment. The measurements of the brightness showed a progressive increase particularly in the control group at days 6, 9, and 12; and in the presence of 1% FN at days 8 and 12.

SEM observations showed different forms of collagen deposition within the collagen sponge Basically there were 3 types of morphologic observations.

Figure 6A:
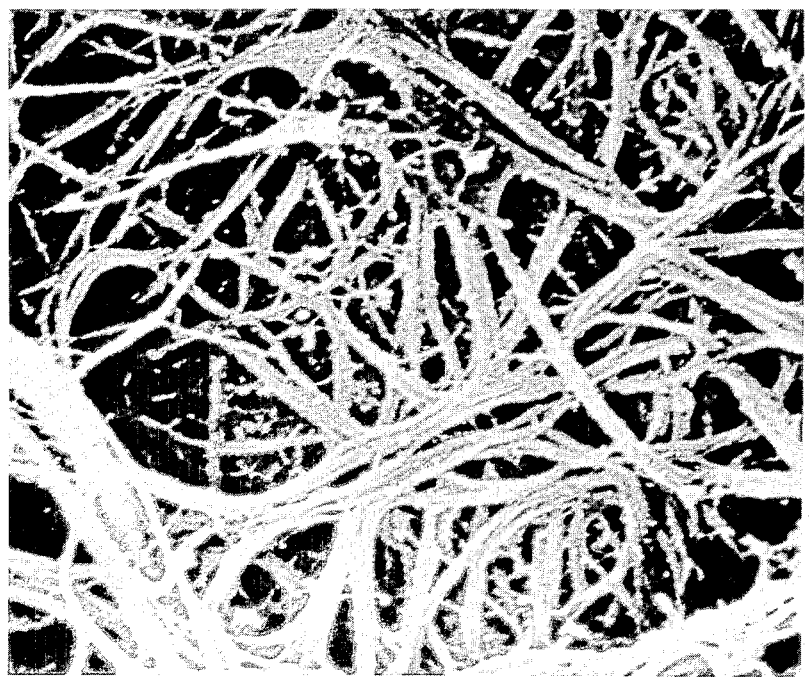
FIG. 6 shows scanning electron micrographs showing newly formed collagen within a collagen-based sponge. (a) At day 6, a thin collagen network is observed in the control collagen sponge where 2 or 3 collagen fibrils are randomly associated. (b) At day 9, collagen fibrils are more densely packed, but disorganized areas are present in the control sponge. (c) At day 9, collagen fibrils are more organized and compact in the presence of hyaluronic acid and fibronectin. (Bar = 1 um).

(1) "Spider-like" morphology where collagen fibrils or thin fibers were spread in all directions; collagen fibers were composed of 2 or 3 collagen fibrils (FIG. 6a) and bridged the inner surface of the pores and channels of the sponge. This morphology was frequently seen at day 6 post implantation either in the control group or in the HAFN collagen sponge.

Figure 6B:
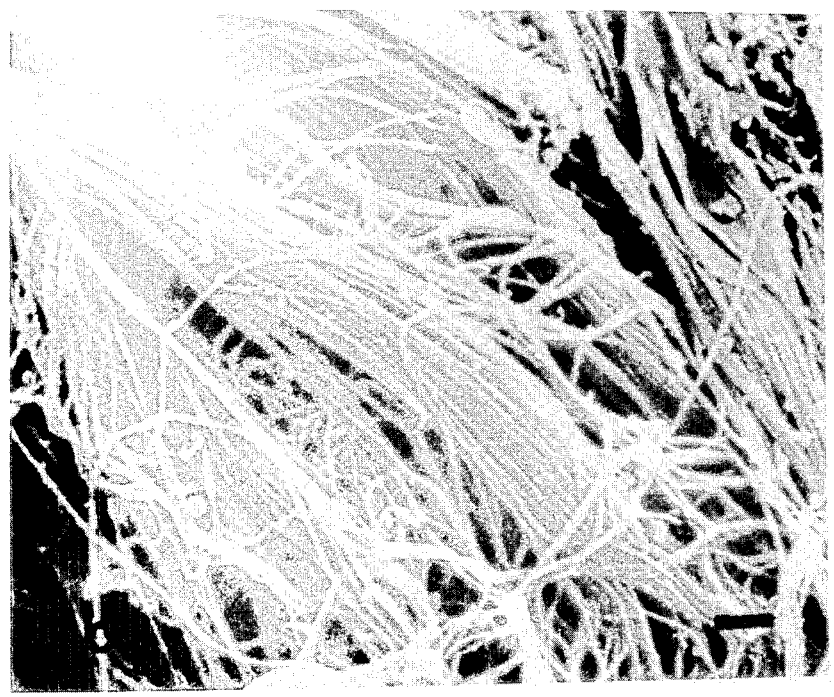

(2) Oriented fibrils aggregated into elongated fibers (FIG. 6b) were observed at days 9 and 12 in control collagen sponges and at days 6, 9, and 12 in the presence of FN and HA.

Figure 6C:
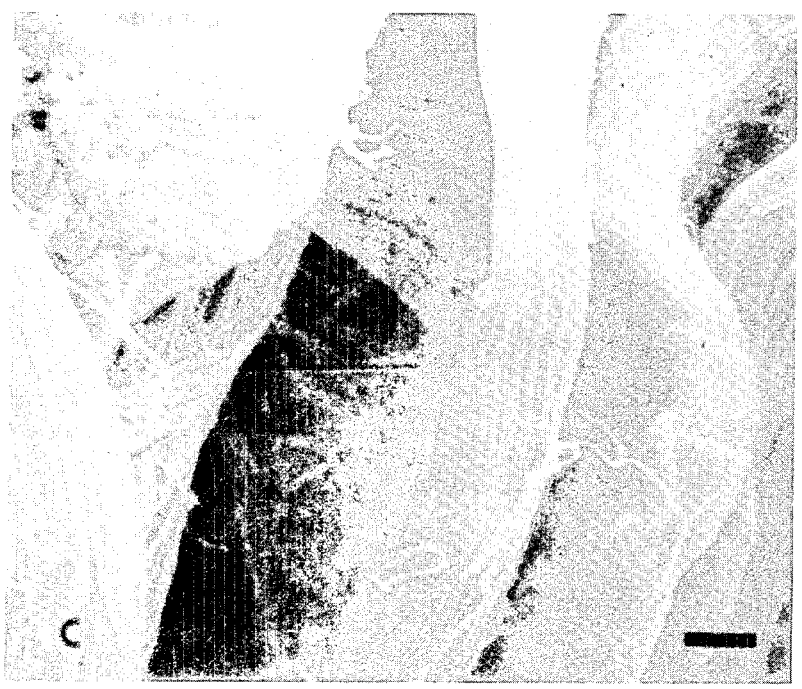

(3) Collagen fibrils densely packed into fibers were observed at days 9 and 12 in the presence of 5% HA and with the HAFN collagen sponge (FIG. 6c). This behavior was particularly apparent at day 12 (FIG. 6c). Measurements of collagen fiber diameter were made on compact fibers as seen in FIG. 6c.

The number of fibroblasts inside the sponge at day 6 was similar for all the sponges, except in the HAFN collagen sponge; at days 6, 9 and 12 it was significantly ($p < 0.0001$) higher than in the control group. The number of fibroblasts was unchanged from days 6 to 12 (Table IV).

The brightness inside the sponge was similar at day 6 for all the sponges. However, the brightness was found significantly ($p < 0.005$) to be higher in the HAFN collagen sponge. A significantly increased amount of birefringent collagen ($p < 0.01$) was observed in the control group as well as in the HAFN collagen sponge between days 6 and 12 (Table V).

Using SEM, observation of fused collagen fibrils into compact fibers was distinct by day 9. However, in a few cases, in the presence of HA and/or FN, collagen fibrils were assembled into thin fibers at day 6. From days 9 to 12, fiber thickness increased without any significant difference between the control group and the HAFN collagen sponge. These results were also observed in the presence of 1% FN or 5% HA alone, but the number of good specimens for SEM observations was not sufficient for statistical analysis Using micrographs of picro-sirius stained tissue sections, collagen fiber diameters increased significantly ($p < 0.005$) from days 9 to 12, but the sponges containing HA and FN did not modify fiber diameters (Table IV).

Birefringence retardation was higher in the collagen sponge containing HA and FN than in the control group ($p < 0.006$), and increased as a function of time ($p < 0.0001$). From days 6 to 9, the birefringence retardation showed a sharp increase. In the presence of 5% HA, a high birefringence retardation was noted, similar to that of the collagen sponge associated with HA and FN, particularly at day 9. Birefringence retardation per unit thickness decreased from days 9 to 12 in the presence of HAFN collagen sponge (Table IV).

TABLE I

Effects of Variations of Freezing Temperature and pH.

| | Freezing Temperatures | | |
|---|---|---|---|
| | −80° C. | −55° C. | −30° C. |
| pHs | D: um, F, P, C, S. | D: um, F, P, C, S. | D: um, F, P, C, S. |
| 2.1 | 14 ± 1, ++, 0, +, 0. | 25 ± 4, +, +, +, 0. | 44 ± 8, 0, ++, 0, ++. |

TABLE I-continued

Effects of Variations of Freezing Temperature and pH.

| | Freezing Temperatures | | |
|---|---|---|---|
| pHs | −80° C. D: um, F, P, C, S. | −55° C. D: um, F, P, C, S. | −30° C. D: um, F, P, C, S. |
| 2.5 | 15 ± 0.5, ++, 0, +, 0. | 22 ± 1, +, +, +, 0. | 47 ± 12, 0, ++, 0, +. |
| 2.7 | 15 ± 0.5, ++, 0, +, 0. | 23 ± 6, +, +, +, 0. | 47 ± 11, 0, ++, +, +. |
| 3.0 | 15 ± 0.7, ++, 0, +, 0. | 29 ± 4, +, +, +, 0. | 68 ± 14, +, +, +, 0. |
| 3.2 | 15 ± 0.7, ++, 0, +, 0. | 33 ± 4, +, +, +, 0. | 69 ± 14, +, +, ++, 0. |
| 3.5 | 14 ± 2, ++, 0, +, 0. | 30 ± 5, +, +, +, 0. | 110 ± 15, +, 0, ++, 0. |

Means and standard deviations of the pore sizes (D: um) as well as a qualitative representation of the surface morphology are presented. Four different surface morphologies are observed by scanning electron microscopy: fibers (F), pores (P), channels (C) and sheet-like structures (S). The abbreviations used to qualitatively assess the presence of fibers, pores, channels, sheet-like structures are (0) none observed, (+) a moderate number of observations, and (++) a large number of observations.

TABLE II

Percentage of ingrowth inside collagen-based sponge at 6, 9, and 12 day post-implantation.

| Specimen | Day 6 % | Day 9 % | Day 12 % |
|---|---|---|---|
| Control collagen sponge | 31 | 48 | 32 |
| Collagen + 1% FN | 12 | 57 | 41 |
| C + 5% FN | 21 | 13 | 7 |
| C + 1% HA | 17 | 20 | 0 |
| C + 5% HA | 64 | 52 | 41 |
| C + 10% HA | 7 | 17 | 4 |
| C + 1% FN + 1% HA | 45 | 88 | 72 |
| C + 1% FN + 5% HA | 11 | 4 | 17 |
| C + 5% FN + 5% HA | 2 | 4 | 5 |

C, Collagen; FN, Fibronectin; HA, Hyaluronic acid.
The ratio is calculated using a qualitative scale from 0 to 4 + by judging the amount of the wound tissue inside the sponge (n − 6 for each period and each tested specimen).

TABLE III

Means and standard errors of the means of the number of fibroblasts per 0.5 mm$^2$ of tissue (A): the percentage of brightness (B) found in the tissue ingrowth after implantion of collagen-based sponges at days 6, 9 and 12.

| | Day 6 | Day 9 | Day 12 |
|---|---|---|---|
| A | | | |
| Control collagen sponge | 69.2 ± 6.9 | 70.4 ± 5.4 | 68.6 ± 6.2 |
| C + 1% FN | 71.2 ± 6.7 | 65.5 ± 5.4 | 72.2 ± 5.8 |
| C + 5% HA | 69.4 ± 5.4 | 61.2 ± 5.8 | 63.5 ± 5.4 |
| C + 1% HA + 1% FN | 97.1 ± 6.9 | 89.0 ± 6.0 | 97.1 ± 5.4 |
| B | | | |
| Control collagen sponge | 6.9 ± 0.8 | 7.7 ± 0.6 | 7.6 ± 0.7 |
| C + 1% FN | 7.5 ± 0.7 | 6.8 ± 0.6 | 10.1 ± 0.6 |
| C + 5% HA | 7.2 ± 0.6 | 8.1 ± 0.6 | 8.8 ± 0.6 |
| C + 1% HA + 1% FN | 7.9 ± 0.7 | 8.8 ± 0.6 | 10.8 ± 0.5 |

Figure 7A:
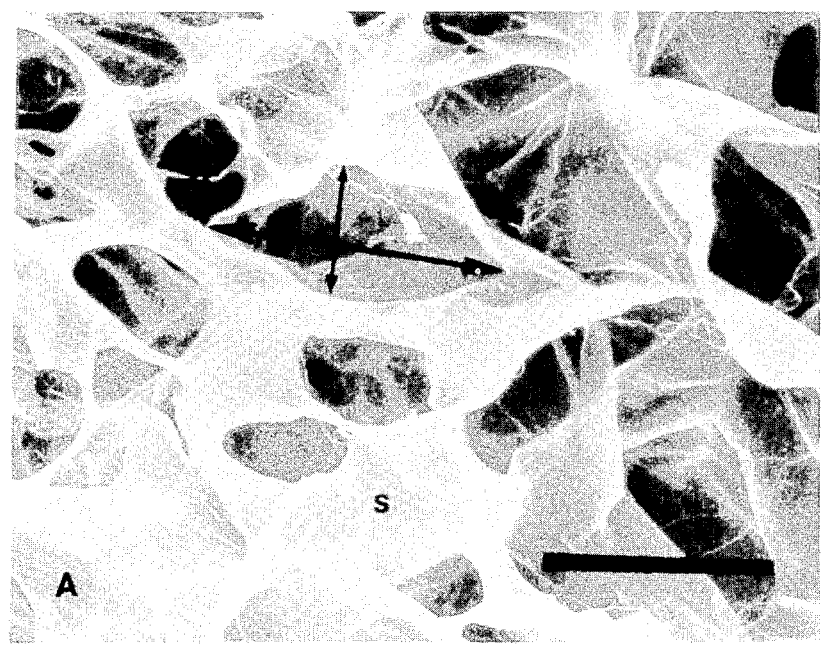
FIG. 7 shows SEMs of a collagen-based sponge before implantation. (A) The porous structure observed is characterized by either superficial pores (s) or deeper pores (d) which provide connections with the deeper layers of the sponge. (B) Deeper pores which form the channels observed are associated with a fibrillar structure (f) of a collagen-based sponge associated with hyaluronic acid and fibronectin. Pore sizes were measured along arrows represented in (A). (Bar = 100 um).
Figure 7B:
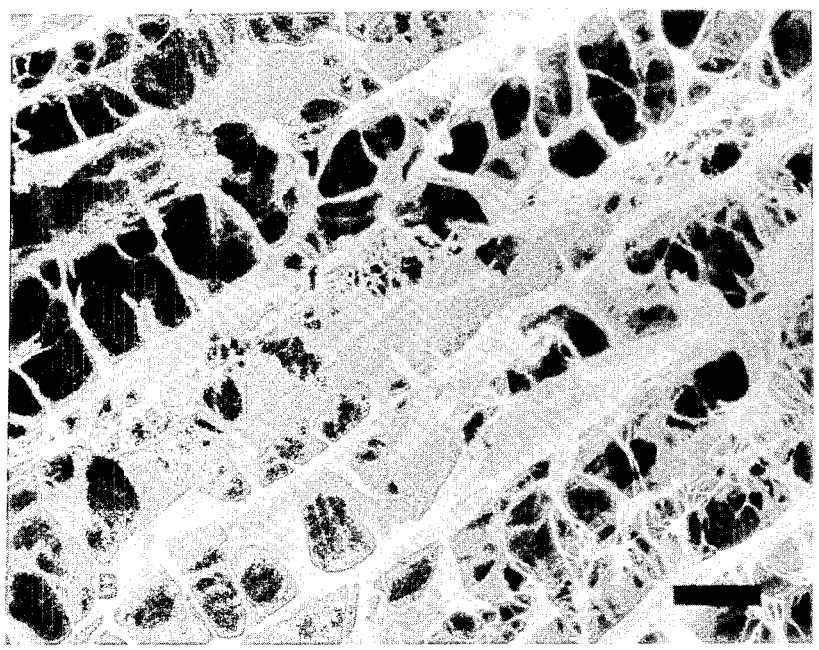

C, Collagen; FN, Fibronectin; HA, Hyaluronic acid.

variety of different types of structures below were frequently observed. Pore structure, defined by SEM, appeared either superficial (FIG. 7A) without connection with deep layers ("superficial pores") or with connections to the deep structure of the sponge ("deep pores") which were termed "channels" (FIG. 7B). Superficial pores were frequently found in the presence of 5% FN and 1% HA, in a few cases superficial pores were found in the presence of 1% HA+1% FN. Deep pores were frequently observed in the presence of 1% HA+1% FN, but also within the control collagen sponge and in the presence of 1% FN, and the fewest deep pores were found in the presence of 1% HA. Channels or deep pores were smooth on their inner surface in almost all cases and particularly in the presence of 1% FN. Formation of fibrous structures (FIG. 7B) was observed on the surface of deep or superficial pores in the presence of 1% HA+1% FN, and 5% HA+1% FN; the lowest frequency was in the presence of 5% HA.

Figure 8A:
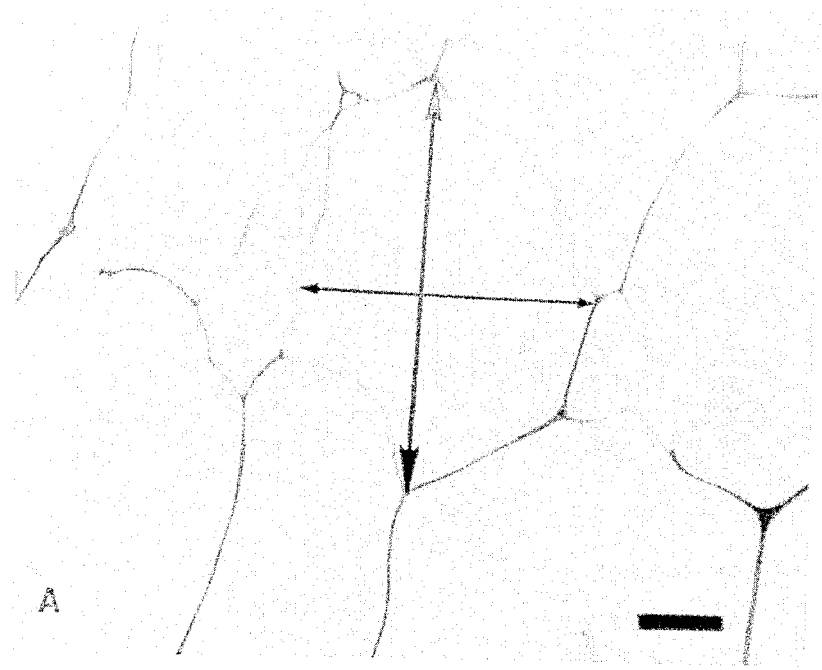
FIG. 8 shows SEMs of plastic embedded collagen sponge sections stained with Azure II-methylene blue. Pores and channels are observed without interchannel communication in a control collagen-based sponge (A): in the presence of hyaluronic acid and fibronectin (B) more connections between channels are observed (large arrows). Pore sizes were measured along two directions (thin arrows) shown in (A). (Bar = 100 um).
Figure 8B:
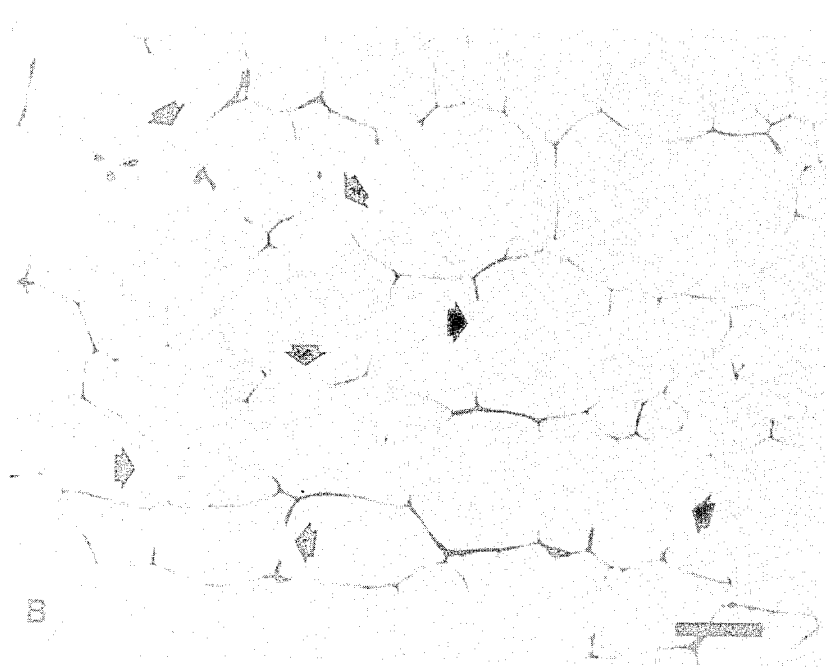

In all cases, plastic embedded sponge sections showed this porous structure (FIG. 8A) which varied between 20 and 200 um (Table V); however, channel structure was regularly observed when HA and FN were both associated at 1% with collagen. In the latter case "open" channels were frequently seen with large interchannel connections (FIG. 8B).

Pore sizes of sponges immersed in a PBS solution after processing for SEM or light microscopy were not significantly different from dried sponges. Pore sizes were also measured on tissue sections after implantation on animals for 6, 9, and 12 days. The average diameter was between 63 and 170 um. This range of pore sizes was found for the control group and for sponges con-

TABLE IV

Results of tissue ingrowth within different collagen sponges.

| | No fibro. 0.5 mm$^2$ | brightness % | fiber 0 (SEM) um | fiber 0 (LM) um | bir. ret. nm | bir. ret. x 10$^3$ fiber 0 |
|---|---|---|---|---|---|---|
| Control SP. | | | | | | |
| day 6 | 69.2 ± 6.9 | 6.9 ± 0.8 | — | — | 9.0 ± 1.8 | — |
| day 9 | 70.4 ± 5.4 | 7.7 ± 0.6 | 2.5 ± 0.5 | 2.7 ± 0.2 | 21.9 ± 1.3 | 8.4 |
| day 12 | 68.6 ± 6.4 | 7.6 ± 0.7 | 3.0 ± 0.6 | 3.2 ± 0.2 | 26.4 ± 1.8 | 8.5 |
| HAFN Coll. SP. | | | | | | |
| day 6 | 97.1 ± 6.9 | 7.9 ± 0.8 | — | — | 17.9 ± 1.4 | — |
| day 9 | 89.0 ± 6.0 | 8.8 ± 0.7 | 2.4 ± 0.5 | 2.1 ± 0.2 | 22.7 ± 1.3 | 10.0 |
| day 12 | 97.1 ± 5.4 | 10.8 ± 0.6 | 3.7 ± 0.6 | 3.5 ± 0.2 | 28.2 ± 1.2 | 7.8 |

Means and standard errors of numbers of fibroblasts (No fibrob.), % of brightness, fiber diameter (0), birefringence retardation (bir. ret) and represented; fiber diameters are determined by scanning electron microscopy (SEM) and by light microscopy (LM). The birefingence retardation per unit fiber thickness is also represented.

Observations by SEM of freeze-dried samples of collagen matrices showed a porous structure with pore sizes between 60 and 250 um (Table V). In all cases, a taining FN and/or HA. These measurements were only made on samples that demonstrated typical tissue ingrowth.

TABLE V

Means and standard deviations of pore sizes found in collagen-based matrices determined by scanning electron microscopy (SEM) and light microscopy (LM)

| Specimen | SEM (um) | LM (um) |
|---|---|---|
| Control collagen sponge | 113 ± 54 | 94 ± 64 |
| Collagen ± 1% FN | 166 ± 73 | 143 ± 84 |
| C + 5% FN | 131 ± 58 | 182 ± 120 |
| C + 1% HA | 188 ± 70 | 201 ± 110 |
| C + 5% HA | 116 ± 47 | 116 ± 84 |
| C + 10% HA | 137 ± 74 | 140 ± 115 |
| C + 1% FN + 1% HA | 125 ± 52 | 149 ± 95 |
| C + 1% FN + 5% HA | 123 ± 59 | 151 ± 85 |
| C + 5% FN + 5% HA | 192 ± 62 | 214 ± 86 |

C, Collagen; FN, Fibronectin; HA, Hyaluronic acid.

The following examples are illustrative of conditions for the process of the present invention and it is to be understood that the scope of the invention is not to be limited thereby.

EXAMPLE 1

Preparation of Soluble and Insoluble Collagens

The collagen used is prepared from calf hides after the grain layer is separated from the corium or dermis. The corium is cut into pieces, washed, swollen, freeze dried and stored at −20° C.

Soluble collagen is obtained by placing 250 gr. of the freeze dried insoluble collagen in 1.5 liters of HCl at a pH of 2.5 containing 1.5 gr. of crystalline pepsin (Sigma Chemical Company). The mixture is stirred overnight at 4° C. and then filtered through cheese cloth, Whatman filter paper #4 followed by Whatman #42, Gelman 5 um and 1.2 um filters and finally through Millipore 0.65 um and 0.45 um filters. The soluble fraction obtained after sequential filtration contains types I, III and V collagens. The soluble collagen fraction is dialyzed against a 1.0 M NaCl solution containing 50 mM Tris adjusted to pH 7.5 and enough solid NaCl is added to raise the molarity of the solution to 1.7. The precipitate at 1.7 M NaCl is type III collagen and is collected by centrifugation at 10,000×g for 60 minutes and then dialyzed versus 0.005 M acetic acid, freeze dried and stored at −20° C. To the supernatant is added additional NaCl to raise the molarity to 2.5 M and the precipitate (type I collagen) is pelleted by centrifugation, dialyzed versus 0.0005 M acetic acid, freeze dried and stored at −20° C. The remaining supernatant contains type V collagen and is dialyzed against 0.005 M acetic acid, freeze dried and stored at −20° C.

Insoluble collagen solutions are obtained by dispersing freeze dried corium ground using a Wiley Mill in HCl at pH of 2.5. The swollen collagen is then dialyzed against 0.005 M acetic acid and freeze dried. If mature bovine hide is the source of the corium, the insoluble collagen produced is typically type I.

Soluble type IV collagen is extracted from the mouse EHS sarcoma tumor after washing the tumor in cold distilled water 3 times by spin filtration at 10,000×g for 30 minutes. The pellet (0.500 gr.) is homogenized in 0.5 liters of 0.5 M acetic acid adjusted to pH 2.5 with HCl and 0.5 gr. of pepsin is added. The homogenate is allowed to mix at 4° C. for 24 to 42 hours, filtered through cheese cloth, spun at 10,000×g for 30 minutes. The pellet is re-suspended in 0.5 M NaCl containing 50 mM Tris, NaCl is added until a final concentration of 4.5 M is obtained, centrifuged at 10,000×g for 30 minutes and the pellet is dialyzed against 0.1 M acetic acid 3 times and freeze dried.

EXAMPLE 2

Preparation of Bovine Serum Fibronectin

Freshly drawn bovine blood (80 ml) is collected in a polypropylene tube containing 20 ml of 5% trisodium citrate and 0.1 mM phenylmethysulfonyl fluoride. The blood is centrifuged at 300×g for 10 minutes and the plasma is then separated from the cell layer and further centrifuged at 30,000×g at a temperature of 15° C. for 30 minutes. To the plasma is then added an additional 1 mM of phenylmethylsulfonyl fluoride and then it is poured through a gelatin-sepharose column. The column is washed with a phosphate buffer solution (0.182 M phosphate and 0.145 M NaCl), 2 column volumes of 1M NaCl in a phosphate buffer, 2 column volumes of phosphate buffer solution, 2 column volumnes of 4 M urea in a phosphate buffer. The optical density of column fractions is monitored at a wavelength of 280 nm with the bulk of the fibronectin normally present in the fractions containing 4 M urea. Fibronectin containing fractions having optical densities greater than 0.1 are dialyzed against 0.180 M phosphate buffer containing 0.145 M NaCl (pH 7.2). The sample is then dialyzed against 0.05 M Tris-HCl containing 4.5 M urea (pH 7.2) and applied to DEAE (diethylaminoethyl cellulose) ion exchange column at room temperature. The column is eluted with a 0 to 0.3 M NaCl linear gradient in a 0.05 M Tris-HCl buffer solution (pH 7.2) containing 4.5 M urea. The eluted fibronectin is dialyzed against 0.180 M phosphate containing 0.145 M NaCl and 1.0 M urea and frozen at −20° C.

EXAMPLE 3

Preparation of Laminin

Laminin is prepared for lathrytic EHS tumors grown in C57/6J mice. The tumors are dissected and homogenized in 3.4 M NaCl containing 50 mM Tris-HCl adjusted to pH 7.4 and protease inhibitors. The homogenate is centrifuged at 16,000×g for 60 minutes the pellet is collected and re-suspended in 3.4 M NaCl. Following centrifugation at 16,000×g for 60 minutes a second time, the homogenate is re-suspended in 0.5 M NaCl containing 50 mM Tris-HCl pH 7.4 and protease inhibitors stirred for 18–24 hours at 4° C. followed by centrifugation at 16,000×g for 60 minutes. The supernatant is brought to 3.5 M by addition of solid NaCl, stirred overnight at 4° C. and the precipitate is collected by centrifugation. Laminin is further purified by redissolving in 0.5 M NaCl containing 50 mM Tris-HCl pH 7.4 followed by centrifugation at 10,000×g for 60 minutes the supernatant is dialyzed against 2 M urea containing 2.5 NaCl and 50 mM Tris-HCl pH 8.6 and chromatographed over a 2.5×2.5 cm column containing DEAE cellulose equilibrated with the same buffer at 4° C. The unbound fraction is dialyzed against 2 M urea containing 50 mM Tris-HCl pH 8.6 and rechromatographed on the DEAE column equilibrated with the same buffer. The unbound fraction is concentrated by vacuum dialysis and chromatographed on Sephacryl S-300 equilibrated with 1.0 MCaCl$_2$, 50 mM Tris-HCl pH 7.5 at 22° C. the void volume is collected and dialyzed against 0.4 M NaCl, 50 mM Tris-HCl pH 7.4 and stored at 4° C. Laminin is resolubilized in 0.1 M ammonium hydroxide pH 11.0 and then the pH is adjusted to 7.2.

EXAMPLE 4

Preparation of Collagen-based Sponges and Sheets

Soluble or insoluble collagen (1.2 gr.) is added to 120 ml of a dilute HCl solution of pH 3.0 and the mixture is ground in a Waring Blender at low speed for 1 minute and thereafter at high speed for 1 minute. The solution or dispersion is then poured into a vacuum flask and deaerated at a vacuum of 100 millitorr for 10 minutes. Collagen dispersions and solutions to be converted into sponges are cooled to 0° C. and frozen at −100° C. before freeze drying at −65° C. under a vacuum of less than 10 millitorr. Collagen dispersion or solutions to be processed into sheets were placed in a sterile hood and allowed to air dry for 24 to 48 hours at 22° C.

EXAMPLE 5

Preparation of Succinylated, Succinimidyl Ester Cross-linked Intermediate Collagen-Based Matrix Nine grams of succinic anhydride are dissolved in 80 ml of distilled water and mixed for 30 minutes at 37° C. After the succinic anhydride is in solution, the pH is adjusted to 7.2 and the volume brought to 100 ml. This solution is placed in a Waring Blender and 1.0 gr. of collagen is added, ground for 2 minutes, allowed to stand at 22° C. for 1 hour, placed on Whatman #4 filter paper to remove unreacted succinic anhydride and then washed with 100 ml of distilled water.

The residue is placed in a solution of 20 ml of phosphate buffer (0.182 M phosphate and 0.145 M NaCl) and 2 gr. of N-hydroxysuccinimide and 2 gr. of cyanamide are added. The solution pH is then adjusted to 7.2. The residue is allowed to react for 3 hours at room temperature and then washed with distilled water in a Buchner funnel under a vacuum of 14 in. of Hg. Sheets and sponges of succinylated, succinimidyl ester cross-linked intermediate collagen-based matrices are produced in accordance with the processes described in Example 4.

EXAMPLE 6

Preparation of Collagen-Based Matrix Containing Fibronectin

To 1.2 gr. soluble or insoluble collagen in 120 ml of HCl pH 3.0 is added to 0.12 gr. of fibronectin in (2.5 mg fibronectin/ml) 0.1 M urea containing 0.182 M phosphate and 0.145 M NaCl and the mixture is dispersed in a Waring Blender for 2 minutes. Sheets and sponges are prepared in accordance with the processes described in Example 4.

EXAMPLE 7

Sponges and Sheets Formed by Coating Type I Collagen With Laminin, Fibronectin, and Type IV Collagen Collagen sheets and sponges formed according to Examples 4 and 6 are swollen in a 0.1 ammonium acetate pH 7.2 containing 1 to 5% laminin, fibronectin or type IV collagen. The swollen sponge or sheet is then frozen and freeze dried at −65° C. and in a vacuum less than 50 millitorr.

EXAMPLE 8

Preparation of Collagen-Based Matrix Containing Hyluronic acid and Proteoglycans To 1.2 gr. of soluble and insoluble collagen in HCl pH 3.0 as added to 0.12 gr. of a complex of hyaluronic acid and proteoglycans (Sigma Chemical Company Grade III-P) in a HCl pH 2.0 to a final volume of 120 ml. The mixture is dispersed in a Waring Blender and either freeze dried or air dried in accordance with the processes of Example 4.

EXAMPLE 9

Preparation of Collagen-Based Matrix Containing Type IV Collagen

To 1.2 gr. of soluble or insoluble collagen type I in HCl pH 2.0 is added to 0.012 gr. of type IV collagen in a 0.1 M ammonium acetate pH 7.2 to a final volume of 120 ml. The mixture is dispersed in a Waring Blender for 2 minutes and formed into sheets or sponges in accordance with the processes of Example 4.

EXAMPLE 10

Cyanamide Cross-Linking of Collagen-Based Matrix

The product of Examples 4 and 6-9 are cross-linked by immersion in an aqueous solution containing 1% by weight of cyanamide at pH 5.5 for a period of 24 hours at 22° C. After removal, the sponges and sheets are exhaustively washed in several changes of water over 24 hours, frozen and freeze dried at −65° C. in a vacuum of less than 50 millitorrs.

EXAMPLE 11

Cross-Linking of Collagen-Based Matrix By Severe Dehydration

The products of Examples 4 and 6-10 are placed in a vacuum oven at room temperature and exposed to a vacuum of less than 50 millitorr. After one hour the samples are heated to 100° C. and remain at this temperature for 72 hours at which time the temperature is lowered to 40° C. The samples are then removed from the vacuum oven and stored at −20° C.

EXAMPLE 12

Cross-Linking of Collagen-Based Matrix Using Succinimidyl Active Ester

Two grams of succinimidyl active ester cross-linked collagen prepared according to Example 5 is placed in a Waring Blender containing 400 ml of HCl pH 2.0 and dispersed for two minutes. This mixture is deaerated by placing in a vacuum of 300 millitorr and is then placed at room temperature in a 100% relative humidity environment for 24 hours. The material is then cooled to 0°C., frozen and freeze dried at −65° C. using a vacuum of less than 50 millitorr or air dried to make sponges or sheets, respectively.

EXAMPLE 13

Preparation of Collagen-Based Matrix Containing Protease Inhibitors

Sponges and sheets prepared according to Examples 4-9 are placed in 20 ml of HCl at pH 2.0 containing 25% cysteine or 0.1% (W/V)2-macroglobulin. The mixture is frozen and freeze dried at −65° C. at a vacuum of less than 50 millitorr or air dried at room temperature.

EXAMPLE 14

In Vitro Enzymatic Degradation

One cm² of each of the products of the above Examples is placed in 2.0 ml of 10 mM Tris-HCl pH 7.4 containing 25 mM calcium chloride and 100 units of type IV collagenase from Clostridium histolyticum (Sigma Chemical Co.) is added per mg of sample. The samples are placed in a 37° C. environment and the intactness of each sample is visually checked every 10 minutes. The time is recorded when each sample has visibly degraded into pieces smaller than about 0.5 um. The results are presented in Table VI.

kg weight was placed on top of the napkins containing the materials for 20 seconds. The wet sample weight was recorded and the sample was then dried at 100° C. for 3 hours. After drying the weight was again recorded and the swelling ratio (r) was calculated from the following relationship:

$$r = 1/V_f$$

where $$V_f = \frac{DW/P_c}{\frac{(DW)}{(P_c)} + \frac{(WW - DW)}{(P_{H20})}} \text{; and where}$$

TABLE VI

Physicochemical Properties of Collagen-Based Carriers

| Carrier Composition | Cross-linking Treatment | Physical Form | r | C.R.T. (min) | Ef | HSM g/mm |
|---|---|---|---|---|---|---|
| Type I Collagen | air dried | Sheet | 22.2 | 72 | 0.37 | 508 |
| Type I Collagen | SD(1) | Sheet | 7.00 | 123 | 0.25 | 850 |
| Type I Collagen | SD(2) | Sheet | 4.11 | 213 | 0.19 | 1058 |
| Type I Collagen | SD(3) | Sheet | 4.20 | 380 | 0.22 | 1468 |
| Type I Collagen | SD(5) | Sheet | 3.13 | 460 | 0.22 | 1048 |
| Type I Collagen | C(1) | Sheet | 5.88 | 105 | 0.42 | 662 |
| Type I Collagen | C(2) | Sheet | 4.48 | 123 | 0.24 | 869 |
| Type I Collagen | C(3) | Sheet | 4.69 | 185 | 0.30 | 990 |
| Type I Collagen | C(4) | Sheet | 4.29 | 237 | 0.35 | 855 |
| Type I Collagen | C(1) + SD(1) | Sheet | 2.75 | 720 | 0.15 | 1186 |
| Type I Collagen | C(1) + SD(2) | Sheet | 2.16 | 960 | 0.16 | 1441 |
| Type I Collagen | C(1) + SD(3) | Sheet | 2.62 | 1440 | 0.12 | 1872 |
| Type I Collagen | SD(3) + C(1) | Sheet | 2.75 | 960 | 0.14 | 1959 |
| Type I Collagen | SD(3) + C(2) | Sheet | 3.03 | 960 | 0.16 | 1833 |
| Type I Collagen | SD(3) + C(3) | Sheet | 3.06 | 960 | 0.11 | 1637 |
| Type I Collagen + 3% HA/PG Complex | air dried | Sheet | 23.3 | 68 | 0.34 | 615 |
| Type I Collagen + 3% HA/PG Complex | SD(3) + C(1) | Sheet | 2.31 | 1440 | 0.15 | 2275 |
| Type I Collagen + 3% HA/PG Complex | C(1) − SD(3) | Sheet | 2.56 | 1440 | 0.13 | 3434 |
| Type I Collagen | P | Sheet | 2.47 | 1515 | | |
| Type I Collagen | P + SD(3) | Sheet | 1.72 | 3180 | | |

Abbreviations:
r = swelling ratio
C.R.T. = collagenase resistance time
SD = severe dehydration at 110° C.
( ) = duration of cross-linking in days
C = 1% cyanamide immersion at 22° C.
HA/PG = hyaluronate-proteoglycan complex (Sigma Chemical Co.)
Ef = strain at failure
HSM = high strain modulus
P = cross-linked using succinyl ester method

EXAMPLE 15

In Vitro Determination of Swelling Ratio

The swelling ratio of denatured collagen is inversely related to the degree of cross-linking. The products of the above Examples were boiled for 2 minutes in distilled water and then blotted between two napkins. A 1 DW and WW are the dry and wet weights, $P_c$ and $P_{H20}$ are the material and water densities, respectively. The results are presented in the aforementioned Table VI.

EXAMPLE 16

Mechanical Properties of Collagen-Based Matrices

Sponges and sheets prepared in accordance with the above Examples were cut into rectangular (4.0 cm × 1.0 cm) strips and immersed in phosphate buffer solution pH 7.5 for 20 minutes prior to mechanical testing. The strips were tested in uniaxial tension at 22° C. at a strain rate of 10%/minute using an Instron Model 1122 testing device. The ends of the strips were placed in pneumatic grips that were closed under a pressure of 40 psig. with a gage length of 20 mm. Stress-strain curves were obtained from which the Young's moduli at high (HSM) and low strains were calculated. The strain at which the low modulus region ended was designated $e_L$ and the strain at failure was denoted $e_f$. The strain results are presented in Table VI, above.

EXAMPLE 17

Subcutaneous Biocompatibility of Collagen-Based Matrix

Sponges and sheets prepared in accordance with the above Examples were tested for biocompatibility subcutaneously after sterilization by exposure of 2.5 M rads of gamma radiation. Implantation was carried out under sterile conditions using 350 gr. white female guinea pigs as test animals.

A 1 cm cutaneous incision was made on one side of the back and the skin was separated from the fascial layer and a 1 cm × 1 cm piece of the implant was placed in this space. The edges of the skin were fastened together over the implant using clips.

Animals were sacrificed on the 6th, 9th and 12th post implantation day and the tissue containing the carrier was placed in Carson's fixative and processed for histological studies. The results are presented in the following Table VII.

TABLE VII

In Vivo Biocompatibility of Collagen-Based Carrier Sponges Implanted Subcutaneously

| Carrier Composition | Cross-linking Treatment | Duration (days) of Implantation | Comments |
|---|---|---|---|
| Type I Collagen | None | 6 | No observable inflammatory response, no ingrowth, implant intact |
| Type I Collagen | None | 9 | No observable inflammatory response, no ingrowth, no intact |
| Type I Collagen | None | 12 | No observable inflammatory response, no ingrowth, implant intact |
| Type I Collagen | SD(3) | 6 | No observable inflammatory response, no ingrowth, implant intact |
| Type I Collagen | C(1) + SD(3) | 6 | No observable inflammatory response, some ingrowth at edges of sponge, implant intact |
| Type I Collagen | C(1) + SD(3) | 9 | No observable inflammatory response, peripheral ingrowth, implant intact |
| Type I Collagen | P | 6 | No observable inflammatory response, no ingrowth, implant intact |
| Type I Collagen | P + SD(3) | 6 | No observable inflammatory response, good ingrowth on periphery, implant intact |

Abbreviations:
P = cross-linked using succinyl ester method
SD = severe dehydration

EXAMPLE 18

Preparation of Diffusion Control Layer on a Matrix Layer

Using sponges and sheets prepared in accordance with the Examples 4–10, a 1 mm layer of Silastic Medical Grade adhesive was applied to the surface of the matrix layer using a spatula. The diffusion control layer is cured by application of a vacuum of 100 millitorr for a period of 2 hours at 22° C. The resultant complex of the diffusion control and matrix layers was placed in contact with full thickness dermal wounds.

EXAMPLE 19

Biocompatibility of Diffusion Control and Matrix Layers on Full Thickness Dermal Wounds Sponges and sheets prepared according to Example 18 were tested after radiation sterilization as dressings on open dermal wounds on female Hartley Albina 350 gr. white guinea pigs. Each animal was separately fed and weighed for 4 days prior to testing One day before testing, the animal was shaved using an electric clipper followed by depilatory treatment with Nair and washed. The animal was then anesthetized by exposure to ether and its back washed with providone-iodine and alcohol solutions. A cm × 2 cm piece of material composed of matrix and diffusion control layers soaked in a phosphate buffer solution (0.182 M phosphate and 0.154 M NaCl), was placed on a full thickness dermal wound on the same area with the matrix layer against the panniculus carnosus. The matrix and the diffusion control layers were sutured to the wound bed at the edges of the dressing using chrome tanned gut sutures. The animal was bandaged by placing sterile cotton dressing sponge over the wound dressing and then wrapped with an Elasticon elastic tape (Johnson and Johnson Products, Inc.) secured around the neck. Animals were housed three to a cage during the experiment.

The animals were monitored daily and their bandages examined for tears. Animals were sacrificed at 6, 9 and 12-day post implantation and the implant and wound beds were excised, fixed and processed for histological examination. The results are presented in Table VIII.

TABLE VIII

In Vivo Biocompatibility of Silicone Coated Collagen-Based Carriers Implanted on Full Thickness Excised Dermal Wounds

| Carrier Composition | Cross-linking Treatment duration in days | Duration (days) of Implantation | Comments |
| --- | --- | --- | --- |
| Type I Collagen | SD(3) | 6 | N.I.R., I.I., fibroblast ingrowth, synthesis of granulation tissue below implant |
| Type I Collagen | SD(3) | 9 | N.I.R., I.I., fibroblast ingrowth, remodeling of granulation tissue within and below implant |
| Type I Collagen | SD(3) | 12 | N.I.R., I.I., extensive fibroblast ingrowth, remodeling of granulation tissue within and below implant |
| Type I Collagen | SD(3)C(1) | 6 | N.I.R., I.I., slight fibroblast ingrowth, granulation tissue formation below implant |
| Type I Collagen | SD(3)C(1) | 9 | N.I.R., I.I., slight fibroblast ingrowth extensive remodeling of granulation tissue below implant |
| Type I Collagen | SD(3)C(1) | 12 | N.I.R., I.I., slight fibroblast ingrowth, extensive remodeling of granulation tissue below implant |
| Type I Collagen | (1)SD(3) | 6 | N.I.R., I.I., slight fibroblast ingrowth, remodeling granulation tissue below implant |
| Type I Collagen | C(1)SD(3) | 9 | N.I.R., I.I., extensive fibroblast ingrowth, granulation tissue within and below implant |
| Type I Collagen | P | 6 | N.I.R., I.I., slight fibroblast ingrowth, granulation tissue below implant |
| Type I Collagen + 1% Laminin | SD(3) | 6 | W.I.R., I.I., slight fibroblast and capillary ingrowth, granulation tissue within and below implant |
| Type I Collagen + 5% Laminin | SD(3) + C(1) | 6 | W.I.R., I.I., extensive capillary ingrowth, granulation tissue within and below implant |
| Type I Collagen + 5% HA/PG | SD(3) + C(1) | 6 | N.I.R., I.I., extensive fibroblast ingrowth, granulation tissue within and below implant |
| Type I Collagen + 5% HA/PG | SD(3) + C(1) | 9 | N.I.R., I.I., extensive fibroblast ingrowth, remodeled granulation tissue below implant |
| Type I Collagen + 5% HA/PG | SD(3) + C(1) | 12 | N.I.R., I.I., implant remodeled after extensive fibroblast ingrowth and migration of epidermis |
| Type I Collagen + 1% Fibronectin + 1% HA/PG | C(1) + SD(3) | 9 | N.I.R., I.I., complete fibroblast ingrowth into sponges remodeled granulation tissue below sponge |
| Type I Collagen + 1% Fibronectin + 1% HA/PG | C(1) + SD(3) | 12 | N.I.R., I.I., implant remodeled after extensive ingrowth and migration of epidermis |
| Type I Collagen + 1% Fibronectin | P | 6 | N.I.R., I.I., extensive fibroblast ingrowth, granulation tissue within implant |
| Type I Collagen + 15 Fibronectin | P | 9 | N.I.R., I.I., extensive fibroblast ingrowth, granulation tissue within implant |
| Type I Collagen + 1% Fibronectin | P | 12 | N.I.R., I.I., partial epidermal migration below implant |
| Type I Collagen + 1% Fibronectin | P + SD(3) | 12 | N.I.R., I.I., extensive fibroblast ingrowth and remodeling of granulation tissue |

Abbreviations:
N.I.R. = no inflammatory response; I.I. — implant intact; W.I.R. = weak inflammatory response; P = cross-linked by succinyl ester formation; SD = severe dehydration; ( ) = duration of cross-linking in days; C = cyanamide treatment; HA/PG = hyaluronate-proteoglycan complex

EXAMPLE 20

Preparation of Collagen Sponges of controlled Pore Size and Morphology

Collagen was extracted from fresh, uncured bovine hides. The collagen was prepared from the chorium of mature bovine hides in a process described by Komanowsky (J. Am. LeatherChem., 69, 410–411, 1974). After liming and washing the collagen was freeze-dried and kept at −30° C. until it was used. Collagen was characterized by sodium dodecyl sulfate polyacrylamide gel electrophoresis and amino acid analysis as typical of type I collagen without non-collagenous protein contamination.

At room temperature, collagen was divided into fine particles using a blender (Osterizer Blender). Collagen was dispersed by blending HCl solution at 0.5 or 1% w/v solids and pHs between 2.0 and 3.75 at different speeds for varying times at room temperature. The dispersion was then deaerated under a vacuum of 300 microns.

Collagen dispersions were poured into plastic or plastic coated metal trays and spread evenly within the trays. Trays with the collagen dispersion were frozen using two sets of conditions: by positioning the tray on a metal plate placed either (1) on a shelf in a freezer which was maintained at −25° C. or (2) in an ethanol bath at temperatures between −20° C. and −90° C. Different temperatures were obtained using the ethanol bath containing dry ice or liquid nitrogen. The frozen dispersion was then placed in the specimen chamber of a freeze-drier (Virtis) which consistently gave a chamber pressure of about 0.1 militorr and a freeze-drying temperature at −60° C.

After freeze-drying, the collagen sponge was cross-linked using a two step process, (Examples 10 and 11). After extensive washing, the sponges were frozen again using either a metal plate placed on the shelf of the freezer at −25° C. or in the ethanol bath at temperatures between −30° C. and −80° C. containing dry ice or liquid nitrogen, and then freeze-dried.

The morphology of different freeze-dried sponges was investigated by scanning electron microscopy (SEM). Freeze-dried specimens were mounted on aluminum studs and coated with an ultra-thin layer of gold in a Polaron E 5300 freeze-drying ion-sputter coating apparatus. These samples were observed in an Amray model 1400 SEM at 30 KV. Using SEM, different types of structure were observed and classified as follows: (1) collagen fibers composed of aggregated collagen fibrils which were dispersed on the surface of sponges; (2) sheet-like structures which formed a flat and smooth surface; and (3) "open pores" characterized by two aspects: surface pores formed from a series of open semi-ellipsoids or semi-spheres with walls that frequently had a sheet-like structure and channels formed from open surface pores that continued into the deeper layers of the sponge. Different areas were photographed, channel and pore sizes were measured, and means and standard deviations were calculated. Fibrillar structures and surface of channels and pores were observed on the micrographs.

Wet collagen sponges were analyzed by SEM following immersion of freeze-dried specimens in a phosphate buffer solution at pH 7.2 for 15 minutes. Hydrated specimens were preserved for SEM analysis by fixation with 2.5% (w/v) glutaraldehyde in cacodylate buffer at pH 7.2, washed in the cacodylate buffer, dehydrated through an increased series of ethanol and acetone, critical point dried against $CO_2$, sputter coated with gold, and observed by SEM. The surface of wet collagen specimens was investigated on scanning electron micrographs as described above.

The interior of collagen sponges was investigated by examination of sections obtained using plastic embedding and sectioning techniques. After complete dehydration in ethanol, the samples were infiltrated for 3 days and embedded in glycol methacrylate (Polysciences JB-4) and three micron sections were cut with a glass knife. Tissue sections were stained with Azure II-Methylene Blue. Micrographs were taken with a light microscope, pore and channel sizes were measured and means and standard deviations were calculated.

EXAMPLE 21

Preparation of HAFN sponge

Collagen-based sponges can be used as a carrier of other connective tissue macromolecules. Fibronectin (FN) extracted from fresh bovine blood as described by Ruoslahti et al. (Methods Enz., 82, 803–831, 1982 and Example 2) and hyaluronic acid (HA) (grade III, potassium salt, from Sigma Chemical Co.) extracted from human umbilical cord were incorporated into collagen sponges. A HCl solution (pH 3.0) containing FN or HA was progressively mixed with the collagen during dispersion. Ratios of 1:99 and 1:19 of FN or HA to collagen (w/w) were tested. Other collagen sponges were made in the same way with both 1% FN and 1% HA; 1% FN and 5% HA; or 5% FN and 5% HA. The top surface of all specimens was coated with a thin layer of silicone and sterilized by gamma irradiation at 2.5 M rads for in vivo studies.

EXAMPLE 22

Animal Studies

A square of 2 by 2 centimeters was excised down to the panniculus carnosus on the back skin of guinea pigs (one wound on each guinea pig). A collagen-based sponge cut to the same dimension as the wound, was sutured into place as previously described (Doillon et al., supra.). Animals were sacrificed at days 6, 9 and 12 post implantation. For each period of time and each collagen sponge tested, 6 animals were used.

EXAMPLE 23

Histology and Scanning Electron Microscopy Preparations

At sacrifice, two pieces of wound tissue containing collagen sponges were excised including pieces of normal skin at both edges. For histology, one specimen was fixed in Carson's buffered formalin, and processed using the routine paraffin embedding. Tissue sections were stained with Hematoxylin and Eosin (H & E), and picro-sirius red (Junqueira et al., 1979, Histochem. J., 11, 447–455).

For SEM, the other piece was fixed in 2.5% (v/v) glutaraldehyde in 0.1 M cacodylate buffer (pH 7.2) for 3 days, and washed in cacodylate buffer for 5 days. The specimens were then dehydrated through a series of ethanol baths and acetone, and critically point dried using $CO_2$. After critical point drying, specimens were fractured through the wound area using forceps, then coated with gold in a sputter coater for 3 minutes at −30° C., and examined in an Amray SEM model 1400 (Bedford, Mass.) at 30 kV.

EXAMPLE 24

Qualitative Data Analysis

H & E stained tissue sections were observed using light microscopy and the frequency and infiltration of tissue ingrowth into the collagen sponge were qualitatively determined. Picro-sirius stained tissue sections were observed under polarized light. In the presence of this stain the birefringence of the newly formed collagen was increased as described by Junqueira et al. (1979, supra.). SEM observations were used to follow the deposition of extracellular collagen as well as collagen fibril assembly into fibers.

The numbers of fibroblasts were determined on H & E stained tissue sections, using micrographs representing approximately 0.5 mm$^2$ of each tissue section from each animal. Cells were considered as fibroblasts based on elongated shape with an elongated nucleus. Cells of at least 3 fields of view were counted on a section through the middle of the wound for each animal.

Brightness of picro-sirius stained tissue sections was used to follow the deposition of collagen in fibers. The degree of brightness was quantitatively determined using a computerized image analysis system. A video camera (Venus TV-2M) mounted on a Leitz polarizing light microscope (12 Pol) was controlled by a Hamamatsu Video Frame Memory (C1140-02, Hamamatsu Systems, Inc., Waltham Mass.). The frame memory was interfaced with a Digital Equipment Corporation PDP-11/03 minicomputer via a RS-232 serial interface. Intensity calibration of the system was done for each histologic slide (to correct for differences in section thickness) by using normal dermis as the "exposure setting". The area for analysis was digitized and integrated using a window. The sum of the intensities of pixels was then divided by the total number of pixels in the window to give the average pixel intensity. The average pixel intensity was divided by the maximum pixel intensity and multipled by 100 to give what was termed the % brightness.

Using polarized light, and a Brace-Kohler compensator ($\lambda/10$ at 546 nm), birefringence retardation was measured on picro-sirius red stained tissue sections by determination of the compensator extinction angle using a video-camera mounted on the microscope. After zeroing the compensator, the fiber to be measured was rotated to a position of maximum extinction, and then oriented diagonally by turning the stage 45°. The determined angle of rotation ($\omega o$) was measured by turning the compensator drum until maximum extinction of the fiber was observed. The phase difference ($\Upsilon$) which is related to the birefringence retardation, was approximated with the following formula.

$$\Gamma = \Gamma o \sin(2 \omega o) \quad (1)$$

where $\Gamma o$ is the polychromatic light calibration value of 71.84 nm.

Collagen fiber diameters were measured from (1) light micrographs taken at 600x on picro-sirius red stained tissue sections and (2) from scanning electron micrographs taken at magnifications between 700x and 10,000x.

Each data point obtained represented the mean of samples ± standard error of the mean; a two-way analysis of variance (Anova) was used to statistically test differences between treatments for each animal.

EXAMPLE 25

Analysis of Morphology of Collagen Matrices

Using scanning electron microscopy (SEM), freeze-dried collagen was analysed in the dry state to observe the morphology of the surface placed in direct contact with the wound tissue. Only the surface in contact with the support during freeze-drying was placed on the wound. Specimens were coated with gold in a Polaron E 5300 freeze-drying ion-sputter apparatus (Polaron Equipment Ltd., Watford, England), and were observed in an Amray SEM model 1400 (Bedford, Mass.) at 30 kV. The largest and the smallest diameters of each pore were measured on micrographs and characterized by calculation of means and standard deviations of pore sizes. In addition, channel and fibrillar structures were characterized on the micrographs using qualitative scales.

Using a plastic embedding technique, the deeper layers of collagen sponges were also investigated. Freeze-dried specimens were immersed in ethanol at 100% (changed twice during 24 h) and then embedded in glycol methacrylate (Polysciences JB-4) (changed 3 times during 48 h). Sections (3 um) were cut with a glass knife and stained with azure II-methylene blue. Micrographs of the different sections were taken with a light microscope ($\times 120$ and $\times 486$) and for each pore and channel, the largest lengths parallel and perpendicular to the surface of the sponge were measured and characterized.

The cross-linked matrices of the invention do not have the inflammatory response which is considered a drawback in the use of collagen for wound repair and coverings. This is accomplished by the dual cross-linking steps and unexpectedly, does not require the use of an additional constituent such as alkaline phosphatase or glycosaminoglycans to eliminate the undesired inflammatory response.

Unexpectedly, compounds having physiological activity, such as hyaluronic acid, fibronectin and other compounds referred to above as carrier compounds can be cross-linked to the collagen matrix and delivered to the wound site. The physiological activity of the compounds is retained even though the compounds have been cross-linked.

Numerous modifications and variations of the present invention are possible in light of the above teachings and, therefore, within the scope of the appended claims, the inventions may be practiced otherwise than as particularly described.

What is claimed:

1. A biodegradable, porous, collagen-based sponge-like composition, especially useful for the treatment of skin wounds, which comprises a biodegradable, three-dimensional matrix of carbodiimide and dehydrothermal cross-linked collagen fibers, wherein the fibers define randomly distributed surface and interior pores which are connected by channels within the iunterior of the sponge, and the channels connect the surface of the composition with the interior of the sponge-like composition, the average pore size being from about 50 to about 250 um, which collagen-based sponge like composition promotes the healing of wounds by fibroblast movement into the channels and pores, attachment of the collagen inside the channels and new tissue formation in the wound.

2. The collagen-based sponge-like structure of claim 1 wherein the matrix is a succinimydyl ester/carbodiimide cross linked matrix, the ester being bifunctional.

3. The collagen-based sponge-like structure of claim 2 wherein the succinimidyl ester is selected from the group consisting of N-hydroxysuccinimide, 3,3-dithio-(sulfosuccinimidyl) propionate and bis(sulfosuccinimidyl) suberate.

4. The collagent-based sponge-like structure of claim 1 wherein the carbodiimide is a cyanamide.

5. The collagen-based sponge-like structure of claim 1 wherein the carbodiimide is selected from the group consisting of cyanamide, and 1-ethyl-3-3(3-dimethylaminopropyl)-carbodiimide hydrochloride.

6. A process for the preparation of the sponge of claim 1 which comprises the steps of
(a) dispersing collagen in an acid solution, at pH from about 3.0 to about 4.0;
(b) freezing the dispersion at about −30° C. to about 50° C.;
(c) freeze-drying the dispersion at about 0.1 millitorr and about −60° C.;
(d) obtaining a collagen sponge having channels of an average pore size of from about 50 um to about 250 um; and,
(e) cross-linking the collagen by two cross-linking steps selected from the group consisting of
(1) contacting the collagen sponge with a cross-linking agent selected from the group consisting of a carbodiimide and a combination of a bifunctional succinimidyl active ester and a carbodiimide and;
(2) subjecting the collagen sponge to elevated temperatures under vacuum.

7. The process of claim 6 wherein step (2) is performed prior to step (1).

8. The process of claim 6 wherein step (1) is performed prior to step (2).

9. The process of claim 6 wherein the acid is HCl.

10. The process of claim 6 wherein the pH is 3.3.

11. The process of claim 6 wherein the freezing temperature is −30° C. to −40° C.

12. A process for the preparation of the sponge of claim 8 which comprises the steps of
(a) dispersing collagen in an acid solution at pH from about 3.0 to about 4.0;
(b) mixing an acid solution containing fibronectin or hyaluronic acid at pH from about 3.0 to about 4.0 with the collagen dispersion;
(c) freezing the dispersion at from about −30° C. to about −50° C.;
(d) freeze-drying the dispersion at about 0.1 millitorr and about −60° C.;
(e) obtaining a collagen sponge having channels and an average pore size of from about 50 um to about 250 um; and,
(f) cross-linking the collagen by two cross-linking steps selected from the group consisting of
(1) contacting the collagen sponge with a cross-linking agent selected from the group consisting of a carbodiimide and a combination of a bifunctional succinimidyl active ester and a carbodiimide and;
(2) subjecting the collagen sponge to elevated temperatures under vacuum.

13. The process of claim 12 wherein step (2) is performed prior to step (1).

14. The process of claim 12 wherein step (1) is performed prior to step (2).

15. The process of claim 12 wherein the acid is HCl.

16. The process of claim 12 wherein the pH is 3.3.

17. The process of claim 12 wherein the freezing temperature is from about −30° C. to about −40° C.

18. A process for the preparation of the sponge of claim 8 which comprises the steps of
(a) dispersing collagen in an acid solution at a pH from about 3.0 to about 4.0;
(b) mixing an acid solution containing fibronectin or hyaluronic acid at pH from about 3.0 to about 4.0 with the collagen dispersion;
(c) freezing the dispersion at from about −30° C. to about −50° C.;
(d) freeze-drying the dispersion at about 0.1 millitorr and about −60° C.;
(e) obtaining a collagen sponge having channels and an average pore size of from about 50 um to about 250 um; and,
(f) cross-linking the collagen by two cross-linking steps selected from the group consisting of
(1) contacting the collagen sponge with a cross-linking agent selected from the group consisting of a carbodiimide and a combination of a bifunctional succinimidyl active ester and a carbodiimide and;
(2) subjecting the collagen sponge to elevated temperatures under vacuum,
(g) suspending the collagen sponge in an acid solution at a pH from about 3.0 to about 4.0, and freezing at from about −30° C. to about −50° C.,
(h) freeze-drying the collagen sponge at about 0.1 millitorr and about −60° C.; and,
(i) obtaining a cross-linked collagen sponge having channels and an average pore size of from about 50 um to about 250 um.

19. The process of claim 18 wherein the acid is HCl.

20. The process of claim 18 wherein the pH is 3.3.

21. The process of claim 18 wherein the temperature is from about −30° C. to about −40° C.

22. The process of claim 18 wherein step (1) is performed prior to step (2).

23. The process of claim 18 wherein step (2) is performed prior to step (1).

24. A biodegradable, porous, collagen-based sponge-like composition, especially useful for the treatment of skin wounds, which comprises a biodegradable, three dimensional matrix of carbodiimide and dehydrothermal cross-linked collagen fibers, wherein the fibers define randomly distributed surface and interior pores which are connected by channels within the interior of the sponge, and the channels connect the surface of the composition with the interior of the sponge-like composition, which collagen-based sponge-like composition promotes the healing of wounds by fibroblast movement into the channels and pores, attachment of the collagent inside the channels and new tissue formation in the wound, and wherein the matrix is cross-linked by a succinimidyl bifunctional ester/carbodiimide or a cyanamide, the matrix includes a fibrillar structure including a connective tissue factor selected from the group consisting of hyaluronic acid and fibronectin, and the pore size is in the range of about 100±50 um.

25. The collagen-based sponge-like structure of claim 24 wherein the matrix is also cyanamide cross-linked.

26. The collagen-based sponge-like structure of claim 24 wherein the succinimydyl ester is selected from the group consisting of N hydroxysuccinimide, 3,3-dithio (sulfosuccinimidyl) propionate and bis (sulfosuccinimidyl) suberate.

27. A biodegradable porous collagen-based sponge-like structure especially useful for the treatment of skin wounds, which comprises a biodegradable collagen fiber network containing hyaluronic acid, fibronectin, or both, wherein the fibers define randomly distributed surface and interior pores which are connected by channels within the interior of the sponge, and the channels connect the surface of the composition with the interior of the sponge-like composition, the average pore size being from about 50 to about 250 um, which collagen-based sponge-like composition promotes the healing of wounds by fibroblast movement into the channels and pores, attachment of the collagen inside the channels and new tissue formation in the wound.

28. A biodegradable, porous, collagen-based sponge-like composition, especially useful for the treatment of skin wounds, which comprises a biodegradable, three-dimensional matrix of dehydrothermal cross-linked collagen fibers, wherein the fibers define randomly distributed surface and interior pores which are connected by channels within the interior sponge, and the channels connect the surface of the composition with the interior of the sponge-like composition, the average pore size being from about 50 to about 250 um, which collagen-based sponge-like composition promotes the healing of wounds by fibroblast movement into the channels and pores, attachment of the collagen inside the channels and new tissue formation in the wound.

29. The collagen-based sponge-like structure of claim 28 positioned in a skin wound, the channels containing fibroblasts and newly formed collagen fibrils.

30. A biodegradable, porous, collagen-based sponge-like composition, especially useful for the treatment of skin wounds, which comprises a biodegradable, three-dimensional matrix of carbodiimide cross-linked collagen fibers, wherein the fibers define randomly distributed surface and interior pores which are connected by channels within the interior of the sponge, and the channels connect the surface of the composition with the interior of the sponge-like composition, the average pore size being from about 50 to about 250 um, which collagen-based sponge-like composition promotes the healing of wounds by fibroblast movement into the channels and pores, attachment of the collagen inside the channels and new tissue formation in the wound.

31. A biodegradable, porous, collagen-based sponge-like composition, especially useful for the treatment of skin wounds, which comprises a biodegradable, three-dimensional matrix of bifunctional succinimidyl active ester cross-linked collagenfibers, wherein the fibers define randomly distributed surface and interior pores which are connected by channels within the interior sponge, and the channels connect the surface of the composition with the interior of the sponge-like composition, the average pore size being from about 50 to about 250 um, which collagen-based sponge-like composition promotes the healing of wounds by fibroblast movement into the channels and pores, attachment of the collagen inside the channels and new tissue formation in the wound.

* * * * *

UNITED STATES PATENT AND TRADEMARK OFFICE
CERTIFICATE OF CORRECTION

PATENT NO. : 4,970,298

DATED : Nov. 13, 1990

INVENTOR(S) : Silver et al.

It is certified that error appears in the above-identified patent and that said Letters Patent is hereby corrected as shown below:

Column 30, line 62, delete "iunterior" and replace by --interior--.
Column 30, line 66, delete "sponge like" and replace by --sponge-like--.
Column 31, line 11, delete "collagent-based" and replace by --collagen-based--.
Column 31, line 22, delete "50°C" and replace by -- -50°C--.
Column 32, line 62, delete "collagent" and replace by --collagen--.
Column 33, line 1, delete "THe" and replace by --The--.

Signed and Sealed this

First Day of December, 1992

*Attest:*

DOUGLAS B. COMER

*Attesting Officer*    *Acting Commissioner of Patents and Trademarks*